US009040772B2

(12) United States Patent
Li et al.

(10) Patent No.: US 9,040,772 B2
(45) Date of Patent: May 26, 2015

(54) COMPOSITIONS AND METHODS FOR ENHANCING RESISTANCE TO NORTHERN LEAF BLIGHT IN MAIZE

(75) Inventors: Bailin Li, Hockessin, DE (US); William A. Wilson, Noblesville, IN (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 172 days.

(21) Appl. No.: 13/696,153

(22) PCT Filed: Jun. 24, 2011

(86) PCT No.: PCT/US2011/041822

§ 371 (c)(1), (2), (4) Date: Nov. 5, 2012

(87) PCT Pub. No.: WO2011/163590

PCT Pub. Date: Dec. 29, 2011

(65) Prior Publication Data

US 2013/0061355 A1 Mar. 7, 2013

Related U.S. Application Data

(60) Provisional application No. 61/358,429, filed on Jun. 25, 2010.

(51) Int. Cl.

| | |
|---|---|
| ***A01H 1/04*** | (2006.01) |
| ***A01H 1/02*** | (2006.01) |
| ***A01H 5/10*** | (2006.01) |
| ***C12N 15/82*** | (2006.01) |
| ***C12Q 1/68*** | (2006.01) |

(52) U.S. Cl.

CPC .............. *A01H 1/04* (2013.01); *C12N 15/8282* (2013.01); *C12Q 1/6895* (2013.01); *C12Q 2600/13* (2013.01); *C12Q 2600/156* (2013.01)

(58) Field of Classification Search

None

See application file for complete search history.

(56) References Cited

U.S. PATENT DOCUMENTS 6,765,132 B1 7/2004 Brenner et al.

FOREIGN PATENT DOCUMENTS

WO 2010/045211 4/2010

OTHER PUBLICATIONS

Wisser et al. (Phytopathology, (2006), vol. 96, No. 2, pp. 120-129).*

Godfrey Asea et al., Validation of Consensus Quantitative Trait Loci Associated with Resistance to Multiple Foliar Pathogens of Maize, Phytopathology, 2009, vol. 99, No. 5, pp. 540-547.

Peter J. Balint-Kurti et al., Use of a Maize Advanced Intercross Line for Mapping of QTL for Northern Leaf Blight Resistance and Multiple Disease Resistance, Crop Science, Mar.-Apr. 2010, vol. 50, pp. 458-466.

Li et al., The physical location of the gene htl (*Helminthosporium turcium* resistance) in maize (*Zea mays L.*), Heredital, 1998, vol. 129, pp. 101-106.

S. Bentolila et al., Identification of an RFLP marker tightly linked to the Ht1 gene in maize, Theor Appl Genet, 1991, vol. 82, pp. 393-398.

Chia-Lin Chung et al., Characteriazation and fine-mapping of a resistance lolcus for northern leaf blight inmaize bin 8.06, Theor Appl Genet, 2010, vol. 121, pp. 205-227.

Manju Gupta et al., Identificat of RFLP markers for the Ht1 gene by comparisonof inbreds and their HT1-conversions, Maize Genetics Cooperation Newsletter 1989.

Kevin D. Simcox et al., Mapping the HtN resistance gene to the long arm of chromosome 8, 1993 Maize Genet Coop Newsletter 67.

Kevin D. Simcox et al., The Use of Molecular Markers to Study *Setosphaeria turcica* Resistance in Maize, Phytopathology, 1993, vol. 82, No. 12, pp. 1326-1330.

Randall J. Wisser et al., Selection Mapping of Loci for Quantitative Disease Resistance in a Diverse Maize Population, Genetics, Sep. 2008, vol. 180, pp. 583-599.

Randall J. Wisser et al., The Genetic Architecture of Disease Resistance in Maize: A Synthesis of Published Studies, Phytopathology, 2006, vol. 96, No. 2, pp. 120-129.

* cited by examiner

*Primary Examiner* — Brent T Page
*Assistant Examiner* — Jared Shapiro

(57) ABSTRACT

The invention relates to methods and compositions for identifying and selecting maize plants with enhanced resistance to northern leaf blight. Maize plants generated by the methods of the invention are also a feature of the invention.

4 Claims, 3 Drawing Sheets

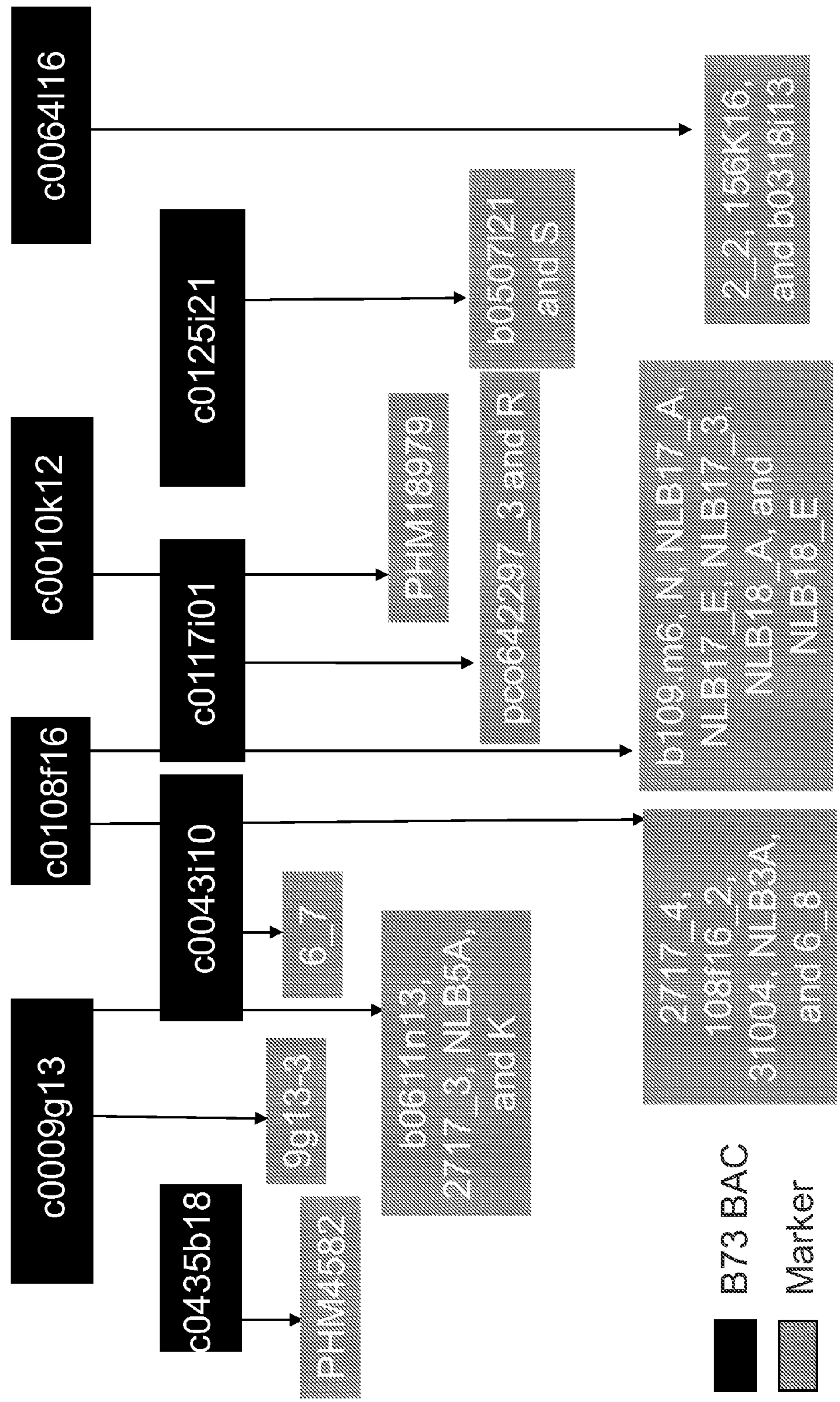
FIG. 1: Chromosome 8 QTL region
c0064l16
c0125i21
c0010k12
c0117i01
c0108f16
c0043i10
c0009g13
c0435b18
2_2, 156K16, and b0318i13
b0507i21 and S
PHM18979
pco642297_3 and R
b109.m6_N, NLB17_A, NLB17_E, NLB17_3, NLB18_A, and NLB18_E
2717_4, 108f16_2, 31004, NLB3A, and 6_8
6_7
b0611n13, 2717_3, NLB5A, and K
9g13-3
PHM4582
B73 BAC
Marker FIG. 2: Annotated PH26N BAC Containing NLB17 and NLB18
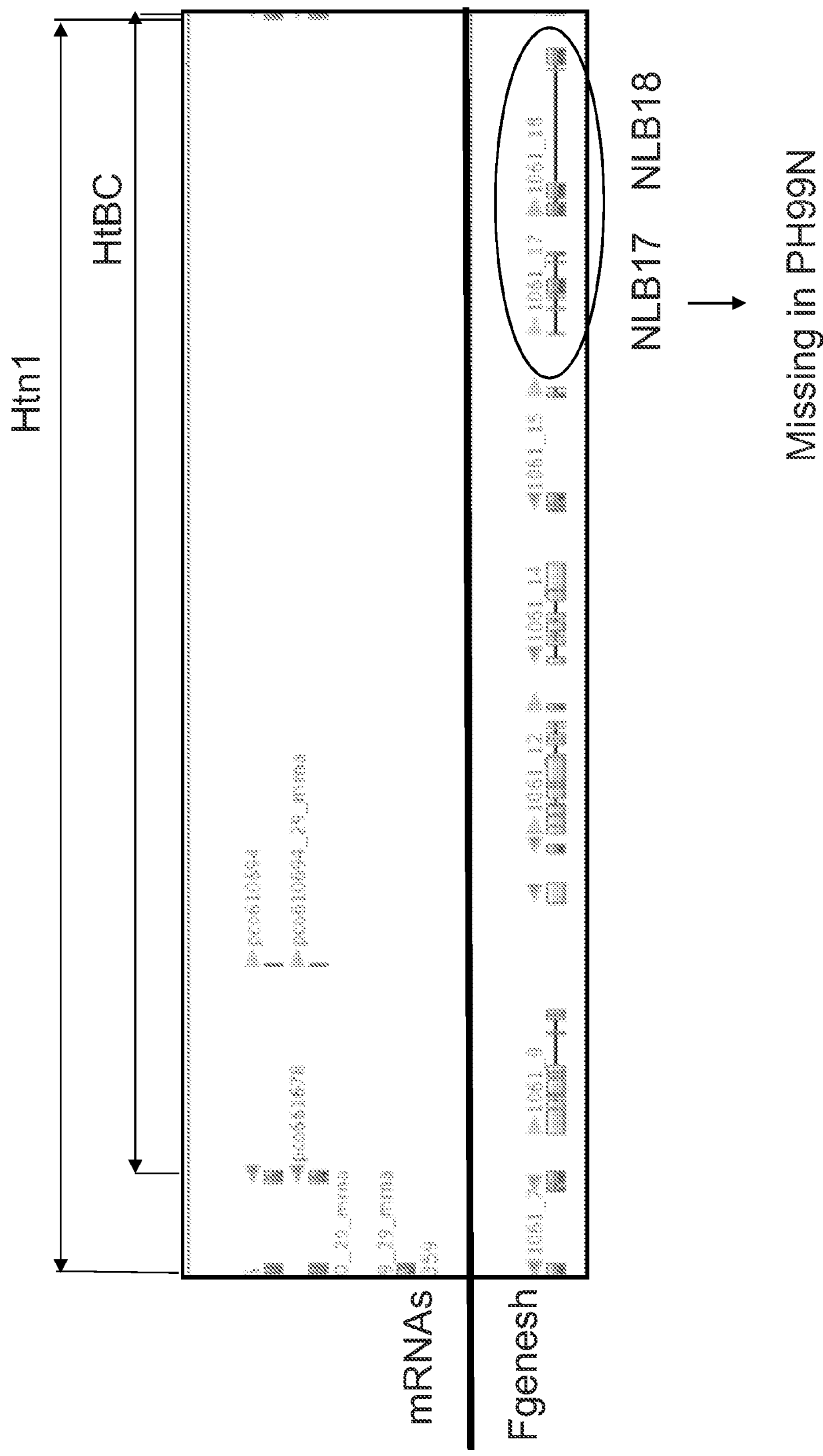

FIG. 3 Scoring guide for northern leaf blight infection in maize
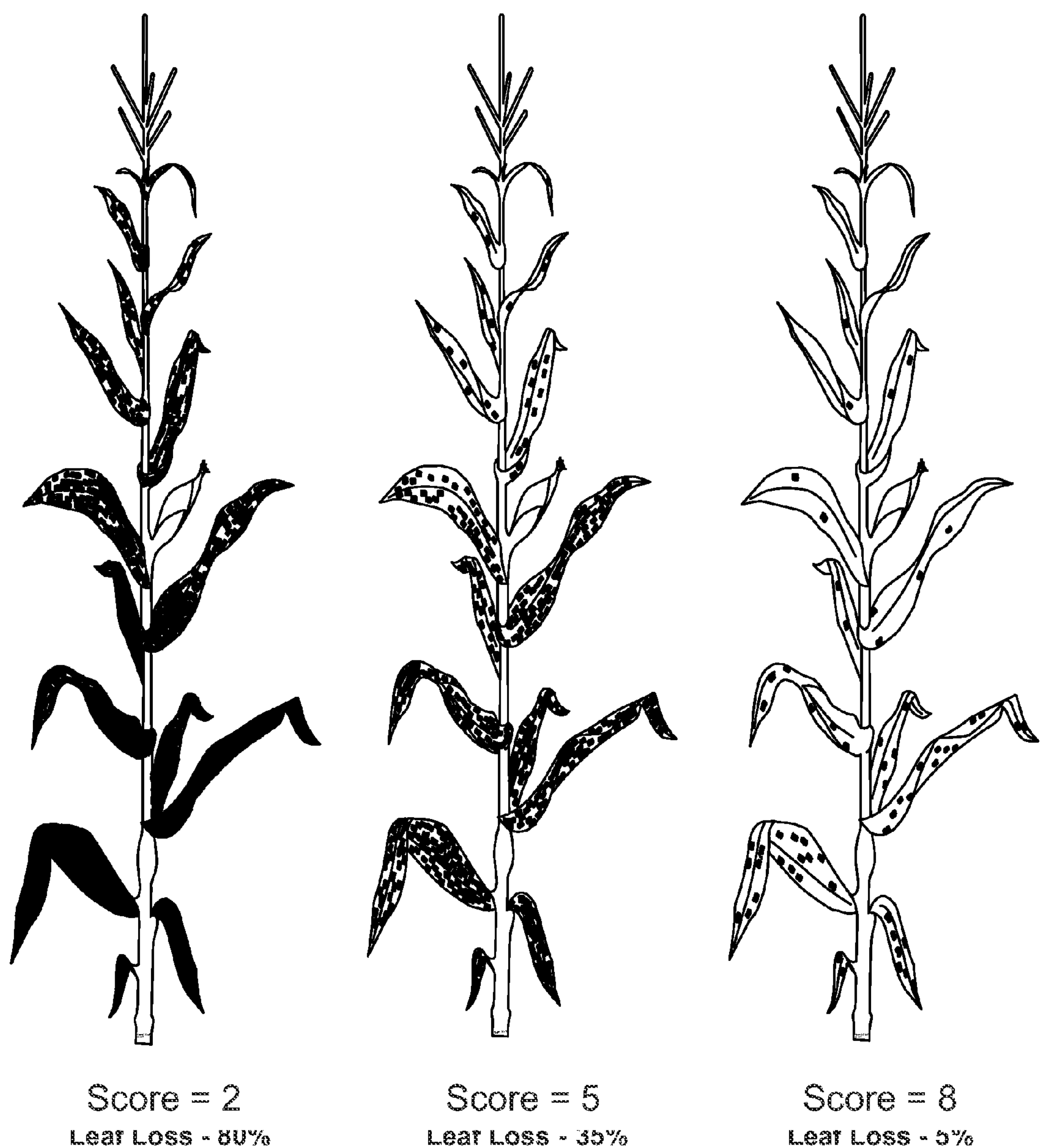

COMPOSITIONS AND METHODS FOR ENHANCING RESISTANCE TO NORTHERN LEAF BLIGHT IN MAIZE

CROSS REFERENCE TO RELATED APPLICATIONS

This application claims the benefit of U.S. Provisional Application No. 61/358,429, filed Jun. 25, 2010, which is incorporated by reference in its entirety.

FIELD OF THE INVENTION

The present disclosure relates to compositions and methods useful in enhancing resistance to northern leaf blight in maize plants.

BACKGROUND OF THE INVENTION

Northern leaf blight (NLB), induced by the fungal pathogen *Exserohilum turcicum* (previously called *Helminthosporium turcicum*), is a serious foliar wilt disease of maize in many tropical and temperate environments. Symptoms can range from cigar-shaped lesions on the lower leaves to complete destruction of the foliage, thereby reducing the amount of leaf surface area available for photosynthesis. A reduction in photosynthetic capability leads to a lack of carbohydrates needed for grain fill, which impacts grain yield. Mid-altitude regions of the tropics, about 900-1600 m above sea level, have a particularly favorable climate for northern leaf blight, as dew periods are long and temperatures moderate. However, northern leaf blight can also yield losses of 30-50% in temperate environments, such as in the United States, during wet seasons, particularly if the infection is established on the upper leaves of the plant by the silking stage.

The fungus *Exserohilum turcicum* (Et) overwinters as mycelia and conidia on maize residues left on the soil surface. The conidia are transformed into resting spores, and during warm, moist weather, new conidia are produced and then carried by wind or rain to lower leaves of young maize plants. Infection requires the presence of water on the leaf surface for 6-18 hours and a temperature of between 66 and 80° F. If infection occurs, lesions develop within 7-12 days and produce new conidia, which spread the infection to secondary sites. Disease management strategies include crop rotation, destruction of old maize residues by tillage, and fungicide application, all of which are aimed at reducing the fungal inoculum. However, the most effective and most preferred method of control for northern leaf blight is the planting of resistant hybrids.

Several varieties or races of *Exserohilum turcicum* are present in nature, leaving growers with two hybrid options: partial resistant hybrids, which offer low-level, broad spectrum protection against multiple races, and race-specific resistant hybrids, which protect against a specific race. Genetic sources of resistance to *Exserohilum turcicum* have been described, and four *Exserohilum turcicum* (previously called *Helminthosporium turcicum*) resistance loci have been identified: Ht1, Ht2, Ht3, and Htn1. Gene Ht1 maps to the long arm of chromosome 2 where it is closely linked to umc36 (Coe, E. H. et al. (1988), *Corn and Corn Improvement,* 3$^{rd}$ *edn*., pp. 81-258), sgcr506 (Gupta, M. et al. (1989) *Maize Genet. Coop. Newsl.* 63, 112), umc150B (Bentolila, S. et al. (1991) *Theor. Appl. Genet.,* 82:393-398), and pic18a (Collins et al. (1998) *Molecular Plant-Microbe Interactions,* 11:968-978), and it is closely flanked by umc22 and umc122 (Li et al. (1998) *Hereditas,* 129:101-106). Gene Ht2 maps to the long arm of chromosome 8 in the umc48-umc89 interval (Zaitlin et al. (1992) *Maize Genet. Coop. Newsl.,* 66, 69-70), and gene Ht3 maps to chromosome 7 near bnlg1666 (Van Staden, D et al. (2001) *Maize Genetics Conference Abstracts* 43:P134). The Htn1 gene maps to chromosome 8, approximately 10 cM distal to Ht2 and 0.8 cM distal to the RFLP marker umc117 (Simcox and Bennetzen (1993) *Maize Genet. Coop. Newl.* 67, 118-119; Simcox and Bennetzen (1993) *Phytopathology,* 83:1326-1330; Chung et al. (2010) *Theor App Gen* Epub).

The methods of controlling northern leaf blight by reducing fungal inoculum require additional time and resources on the part of the farmer, and in addition, can have detrimental effects on the environment. This makes the planting of resistant hybrids even more attractive to farmers and the general public. Thus, it is desirable to provide compositions and methods for identifying and selecting maize plants with enhanced resistance to northern leaf blight. These plants can be used in breeding programs to generate high-yielding hybrids with resistance to northern leaf blight.

SUMMARY

Compositions and methods for identifying and selecting maize plants with enhanced resistance to northern leaf blight are provided.

In one embodiment, methods of selecting maize plants with enhanced resistance to northern leaf blight are presented. The methods include detecting one or more marker alleles in the maize plant that are linked to and associated with: the PH26N haplotype at NLB17_A, the PH26N haplotype at NLB17_E, the PH26N haplotype at NLB17__3, the PH26N haplotype at NLB18_A, the PH26N haplotype at NLB18_E, the PH99N haplotype at NLB18_A, or the PH99N haplotype at NLB18_E. A maize plant that has the one or more marker alleles linked to and associated with any of the haplotypes listed above is then selected as having enhanced northern leaf blight resistance.

In another embodiment, the marker allele can be linked to any of the following haplotypes: the PH26N haplotype at NLB17_A, the PH26N haplotype at NLB17_E, the PH26N haplotype at NLB17__3, the PH26N haplotype at NLB18_A, the PH26N haplotype at NLB18_E, the PH99N haplotype at NLB18_A, or the PH99N haplotype at NLB18_E by 30 cM, 25, 20, 15, 10, 9, 8, 7, 6, 5, 4, 3, 2, 1, 0.9, 0.8, 0.7, 0.6, 0.5, 0.4, 0.3, 0.2, or 0.1 cM.

In another embodiment, methods of selecting maize plants with enhanced resistance to northern leaf blight are presented. The methods include detecting a haplotype in the maize plant wherein the haplotype can be any of the following: the PH26N haplotype at NLB17_A, the PH26N haplotype at NLB17_E, the PH26N haplotype at NLB17__3, the PH26N haplotype at NLB18_A, the PH26N haplotype at NLB18_E, the PH99N haplotype at NLB18_A, or the PH99N haplotype at NLB18_E. A maize plant that has the haplotype is then selected as having enhanced northern leaf blight resistance.

In another embodiment, methods for identifying maize plants with enhanced resistance to northern leaf blight by detecting at least one marker allele associated with the enhanced resistance in the germplasm of a maize plant are provided. The marker locus can be selected from any of the following marker loci: PHM2798, b0302H1, b0611N13, 2717__3, 2717__4, 108f16__2, 31004, pco642297__3, b109.m6, PHM18979, b0507L21, 2__2, 156K16, b0318i13, PHM4757, PHM13395-27, PHM4677-11, PHM3418-12, PHM15992-3, NLB5A, NLB3A, PHM4582, 9g13-3, K, 6__7, 6__8, N, R, S, U, PHM2817-26, PHM7446-6, PHM13395-16, NLB17_A, NLB17_E, NLB17__3, NLB18_A, or NLB18_E; as well as any other marker that is linked to these markers. The marker locus comprises at least one allele that is associated with enhanced resistance to northern leaf blight. Maize plants identified by this method are also of interest.

In another embodiment, methods for identifying maize plants with enhanced resistance to northern leaf blight by detecting a haplotype in the germplasm of the maize plant, wherein the haplotype is associated with enhanced resistance to northern leaf blight, are provided. The haplotype comprises alleles at one or more marker loci, wherein the one or more marker loci are found within an interval on chromosome 8 comprising and flanked by:

i. markers PHM4582 and R, or ii. markers 6__8 and R.

In another embodiment, the haplotype is the PH26N haplotype at NLB17_A, the PH26N haplotype at NLB17_E, the PH26N haplotype at NLB17__3, the PH26N haplotype at NLB18_A, the PH26N haplotype at NLB18_E, the PH99N haplotype at NLB18_A, or the PH99N haplotype at NLB18_E.

In another embodiment, methods of selecting plants with enhanced resistance to northern leaf blight are provided. In one aspect, a first maize plant is obtained that has the PH26N haplotype at NLB17_A, the PH26N haplotype at NLB17_E, the PH26N haplotype at NLB17__3, the PH26N haplotype at NLB18_A, the PH26N haplotype at NLB18_E, the PH99N haplotype at NLB18_A, or the PH99N haplotype at NLB18_E. The first maize plant can then be crossed to a second maize plant, and the progeny plants resulting from the cross can be evaluated for the presence of the haplotype. Progeny plants that possess the haplotype of the first maize plant can be selected as having enhanced resistance to northern leaf blight. Progeny plants selected by this method are also of interest.

In another embodiment, the invention concerns an isolated polynucleotide comprising: (a) at least one nucleotide sequence encoding a polypeptide capable of conferring or enhancing resistance to northern leaf blight, wherein the polypeptide has an amino acid sequence of at least 90% sequence identity, based on the Clustal V method of alignment, when compared to SEQ ID NO:93, 95, or 97; or (b) a full complement of the nucleotide sequence, wherein the full complement and the nucleotide sequence consist of the same number of nucleotides and are 100% complementary. The polypeptide may comprise the amino acid sequence of SEQ ID NO:93, 95, or 97. The nucleotide sequence may comprise the nucleotide sequence of SEQ ID NO:92, 94, or 96.

In another embodiment, the invention concerns a vector comprising the claimed isolated polynucleotide.

In another embodiment, the invention concerns a recombinant DNA construct comprising the isolated polynucleotide of the invention operably linked to at least one regulatory sequence.

In another embodiment, the invention concerns a maize cell comprising the recombinant DNA construct or the isolated polynucleotide of the invention.

In another embodiment, the invention concerns a process for producing a maize plant comprising transforming a plant cell with the recombinant DNA construct of the invention and regenerating a plant from the transformed plant cell.

In another embodiment, the invention concerns a maize plant comprising the recombinant DNA construct of the invention.

In another embodiment, the invention concerns a maize seed comprising the recombinant DNA construct of the invention.

In another embodiment, the invention concerns a process of conferring or improving resistance to northern leaf blight, comprising transforming a plant with the recombinant DNA construct of the invention, thereby conferring or improving resistance to northern leaf blight.

In another embodiment, the invention concerns a process of determining the presence or absence of the polynucleotide of the invention in a maize plant, comprising at least one of:

(a) isolating nucleic acid molecules from said maize plant and amplifying sequences homologous to the polynucleotide of the invention, or (b) isolating nucleic acid molecules from said maize plants and performing a Southern hybridization, or (c) isolating proteins from said maize plant and performing a western blot using antibodies to the protein, or (d) isolating proteins from said maize plant and performing an ELISA assay using antibodies to the protein, or (e) demonstrating the presence of mRNA sequences derived from the mRNA transcript and unique to the northern leaf blight resistance locus, thereby determining the presence of the polynucleotide of the invention in said maize plant.

In another embodiment, the invention concerns a process of determining the presence or absence of the northern leaf blight resistance locus in a maize plant, comprising at least one of:

(a) isolating nucleic acid molecules from said maize plant and amplifying sequences unique to the polynucleotide of the invention, or (b) isolating proteins from said maize plant and performing a western blot using antibodies to the protein, or (c) isolating proteins from said maize plant and performing an ELISA assay using antibodies to the protein, or (d) demonstrating the presence of mRNA sequences derived from the mRNA transcript and unique to the northern leaf blight resistance locus, thereby determining the presence of the northern leaf blight resistance locus in said maize plant.

In another embodiment, the invention concerns a process of altering the level of expression of a protein capable of conferring resistance to northern leaf blight a maize cell comprising:

(a) transforming a maize cell with the recombinant DNA construct of the invention and (b) growing the transformed maize cell under conditions that are suitable for expression of the recombinant DNA construct wherein expression of the recombinant DNA construct results in production of altered levels of a protein capable of conferring resistance to northern leaf blight in the transformed maize cell when compared to levels of expression in a wild-type maize plant having resistance to northern leaf blight.

In another embodiment, the invention concerns a process of altering the level of expression of a protein capable of conferring resistance to northern leaf blight in a maize cell comprising:

(a) transforming a maize cell with the recombinant DNA construct of the invention; and (b) growing the transformed maize cell under conditions that are suitable for expression of the recombinant DNA construct wherein expression of the recombinant DNA construct results in production of altered levels of a protein capable of conferring resistance to northern leaf blight in the transformed maize cell when compared to levels of expression in a wild-type maize plant having resistance to northern leaf blight.

In another embodiment, the invention concerns a process of altering the level of expression of a protein capable of conferring resistance to northern leaf blight in a maize plant comprising:

(a) transforming a maize plant cell with the recombinant DNA construct of the invention; and (b) regenerating a transformed maize plant from the transformed maize plant cell; and (c) growing the transformed maize plant under conditions that are suitable for expression of the recombinant DNA construct wherein expression of the recombinant DNA construct results in production of altered levels of a protein capable of conferring resistance to northern leaf blight in the transformed maize plant when compared to levels of expression in a wild-type maize plant having resistance to northern leaf blight.

In another embodiment, the invention concerns a process of altering the level of expression of a protein capable of conferring resistance to northern leaf blight in a maize plant comprising:

(a) transforming a maize plant cell with the recombinant DNA construct of the invention; and (b) regenerating the transformed maize plant from the transformed maize plant cell; and (c) growing the transformed maize plant under conditions that are suitable for expression of the recombinant DNA construct wherein expression of the recombinant DNA construct results in production of altered levels of a protein capable of conferring resistance to northern leaf blight in the transformed maize plant when compared to levels of expression in a wild-type maize plant having resistance to northern leaf blight.

BRIEF DESCRIPTION OF DRAWINGS AND SEQUENCE LISTINGS

The invention can be more fully understood from the following detailed description and the accompanying drawings and Sequence Listing which form a part of this application. The Sequence Listing contains the one letter code for nucleotide sequence characters and the three letter codes for amino acids as defined in conformity with the IUPAC-IUBMB standards described in Nucleic Acids Research 13:3021-3030 (1985) and in the Biochemical Journal 219 (No. 2): 345-373 (1984), which are herein incorporated by reference in their entirety. The symbols and format used for nucleotide and amino acid sequence data comply with the rules set forth in 37 C.F.R. §1.822.

FIG. 1 shows the physical map arrangement of sequenced BACs (obtained from the Maize Genome Sequencing Project) in the chromosome 8 region where a QTL associated with northern leaf blight is located. The positions of the markers described herein that can be used for marker-assisted selection (MAS) are indicated.

FIG. 2 shows the arrangement of mRNAs and Fgenesh-predicted open reading frames in an annotated PH26N BAC. The NLB17 and NLB18 Fgenesh-predicted open reading frames, representing putative protein kinases, are indicated.

FIG. 3 shows the diagram used as a guide to score northern leaf blight infection.

The sequence descriptions and Sequence Listing attached hereto comply with the rules governing nucleotide and/or amino acid sequence disclosures in patent applications as set forth in 37 C.F.R. §1.821-1.825. The Sequence Listing contains the one letter code for nucleotide sequence characters and the three letter codes for amino acids as defined in conformity with the IUPAC-IUBMB standards described in *Nucleic Acids Res.* 13:3021-3030 (1985) and in the *Biochemical J.* 219 (2):345-373 (1984) which are herein incorporated by reference. The symbols and format used for nucleotide and amino acid sequence data comply with the rules set forth in 37 C.F.R. §1.822.

SEQ ID NO:1 is the sequence of the PHM2798 forward primer.

SEQ ID NO:2 is the sequence of the PHM2798 reverse primer.

SEQ ID NO:3 is the sequence of the b0302H1 forward primer.

SEQ ID NO:4 is the sequence of the b0302H1 reverse primer.

SEQ ID NO:5 is the sequence of the b0611N13 forward primer.

SEQ ID NO:6 is the sequence of the b0611N13 reverse primer.

SEQ ID NO:7 is the sequence of the 2717_3 forward primer.

SEQ ID NO:8 is the sequence of the 2717_3 reverse primer.

SEQ ID NO:9 is the sequence of the 2717_4 forward primer.

SEQ ID NO:10 is the sequence of the 2717_4 reverse primer.

SEQ ID NO:11 is the sequence of the 108f16_2 forward primer.

SEQ ID NO:12 is the sequence of the 108f16_2 reverse primer.

SEQ ID NO:13 is the sequence of the 31004 forward primer.

SEQ ID NO:14 is the sequence of the 31004 reverse primer.

SEQ ID NO:15 is the sequence of the pco642297_3 forward primer.

SEQ ID NO:16 is the sequence of the pco642297_3 reverse primer.

SEQ ID NO:17 is the sequence of the b109.m6 forward primer.

SEQ ID NO:18 is the sequence of the b109.m6 reverse primer.

SEQ ID NO:19 is the sequence of the PHM18979 forward primer.

SEQ ID NO:20 is the sequence of the PHM18979 reverse primer. SEQ ID NO:21 is the sequence of the b0507L21 forward primer.

SEQ ID NO:22 is the sequence of the b0507L21 reverse primer.

SEQ ID NO:23 is the sequence of the 2_2 forward primer.

SEQ ID NO:24 is the sequence of the 2_2 reverse primer.

SEQ ID NO:25 is the sequence of the 156K16 forward primer.

SEQ ID NO:26 is the sequence of the 156K16 reverse primer.

SEQ ID NO:27 is the sequence of the b0318i13 forward primer.

SEQ ID NO:28 is the sequence of the b0318i13 reverse primer.

SEQ ID NO:29 is the sequence of the PHM4757 forward primer.

SEQ ID NO:30 is the sequence of the PHM4757 reverse primer.

SEQ ID NO:31 is the sequence of the NLB5A forward primer.

SEQ ID NO:32 is the sequence of the NLB5A reverse primer.

SEQ ID NO:33 is the sequence of the NLB5A probe.

SEQ ID NO:34 is the sequence of the NLB3A forward primer.

SEQ ID NO:35 is the sequence of the NLB3A reverse primer.

SEQ ID NO:36 is the sequence of the NLB3A probe.

SEQ ID NO:37 is the sequence of the PHM2817-26 forward primer.

SEQ ID NO:38 is the sequence of the PHM2817-26 reverse primer.

SEQ ID NO:39 is the sequence of the PHM7446-6 forward primer.

SEQ ID NO:40 is the sequence of the PHM7446-6 reverse primer.

SEQ ID NO:41 is the sequence of the PHM4582 forward primer.

SEQ ID NO:42 is the sequence of the PHM4582 reverse primer.

SEQ ID NO:43 is the sequence of the 9g13-3 forward primer.

SEQ ID NO:44 is the sequence of the 9g13-3 reverse primer.

SEQ ID NO:45 is the sequence of the K forward primer.

SEQ ID NO:46 is the sequence of the K reverse primer.

SEQ ID NO:47 is the sequence of the 6__7 forward primer.

SEQ ID NO:48 is the sequence of the 6__7 reverse primer.

SEQ ID NO:49 is the sequence of the 6__8 forward primer.

SEQ ID NO:50 is the sequence of the 6__8 reverse primer.

SEQ ID NO:51 is the sequence of the N forward primer.

SEQ ID NO:52 is the sequence of the N reverse primer.

SEQ ID NO:53 is the sequence of the R forward primer.

SEQ ID NO:54 is the sequence of the R reverse primer.

SEQ ID NO:55 is the sequence of the S forward primer.

SEQ ID NO:56 is the sequence of the S reverse primer.

SEQ ID NO:57 is the sequence of the U forward primer.

SEQ ID NO:58 is the sequence of the U reverse primer.

SEQ ID NO:59 is the sequence of the PHM13395-16 forward primer.

SEQ ID NO:60 is the sequence of the PHM13395-16 reverse primer.

SEQ ID NO:61 is the sequence of the PHM3418-12 forward primer.

SEQ ID NO:62 is the sequence of the PHM3418-12 reverse primer.

SEQ ID NO:63 is the sequence of the PHM13395-27 forward primer.

SEQ ID NO:64 is the sequence of the PHM13395-27 reverse primer.

SEQ ID NO:65 is the sequence of the PHM4677-11 forward primer.

SEQ ID NO:66 is the sequence of the PHM4677-11 reverse primer.

SEQ ID NO:67 is the sequence of the PHM15992-3 forward primer.

SEQ ID NO:68 is the sequence of the PHM15992-3 reverse primer.

SEQ ID NO:69 is the sequence of the NLB17_A forward primer.

SEQ ID NO:70 is the sequence of the NLB17_A reverse primer.

SEQ ID NO:71 is the sequence of the NLB17_E forward primer.

SEQ ID NO:72 is the sequence of the NLB17_E reverse primer.

SEQ ID NO:73 is the sequence of the NLB17__3 forward primer.

SEQ ID NO:74 is the sequence of the NLB17__3 reverse primer.

SEQ ID NO:75 is the sequence of the NLB18_A forward primer.

SEQ ID NO:76 is the sequence of the NLB18_A reverse primer.

SEQ ID NO:77 is the sequence of the NLB18_E forward primer.

SEQ ID NO:78 is the sequence of the NLB18_E reverse primer.

SEQ ID NO:79 is the sequence of the tail added to F primers of the NLB17 and NLB18 marker sets.

SEQ ID NO:80 is the sequence of the tail added to R primers of the NLB17 and NLB18 marker sets.

SEQ ID NO:81 is the PHM13395 reference sequence.

SEQ ID NO:82 is the PHM4677 reference sequence.

SEQ ID NO:83 is the PHM3418 reference sequence.

SEQ ID NO:84 is the PHM15992 reference sequence.

SEQ ID NO:85 is the PHM2817 reference sequence.

SEQ ID NO:86 is the PHM7446 reference sequence.

SEQ ID NO:87 is the NLB17_A reference sequence.

SEQ ID NO:88 is the NLB17_E reference sequence.

SEQ ID NO:89 is the NLB17__3 reference sequence.

SEQ ID NO:90 is the NLB18_A reference sequence.

SEQ ID NO:91 is the NLB18_E reference sequence.

SEQ ID NO:92 is the NLB17 cDNA sequence from PH26N.

SEQ ID NO:93 is the amino acid sequence of the protein encoded by SEQ ID NO:92.

SEQ ID NO:94 is the NLB18 cDNA sequence from PH99N.

SEQ ID NO:95 is the amino acid sequence of the protein encoded by SEQ ID NO:94.

SEQ ID NO:96 is the NLB18 cDNA sequence from PH26N.

SEQ ID NO:97 is the amino acid sequence of the protein encoded by SEQ ID NO:96.

DETAILED DESCRIPTION

The present invention provides allelic compositions in maize and methods for identifying and selecting maize plants with enhanced resistance to northern leaf blight. The following definitions are provided as an aid to understand this invention.

The term “allele” refers to one of two or more different nucleotide sequences that occur at a specific locus.

“Allele frequency” refers to the frequency (proportion or percentage) at which an allele is present at a locus within an individual, within a line, or within a population of lines. For example, for an allele “A”, diploid individuals of genotype “AA”, “Aa”, or “aa” have allele frequencies of 1.0, 0.5, or 0.0, respectively. One can estimate the allele frequency within a line by averaging the allele frequencies of a sample of individuals from that line. Similarly, one can calculate the allele frequency within a population of lines by averaging the allele frequencies of lines that make up the population. For a population with a finite number of individuals or lines, an allele frequency can be expressed as a count of individuals or lines (or any other specified grouping) containing the allele.

An “amplicon” is an amplified nucleic acid, e.g., a nucleic acid that is produced by amplifying a template nucleic acid by any available amplification method (e.g., PCR, LCR, transcription, or the like).

The term “amplifying” in the context of nucleic acid amplification is any process whereby additional copies of a selected nucleic acid (or a transcribed form thereof) are produced. Typical amplification methods include various polymerase based replication methods, including the polymerase chain reaction (PCR), ligase mediated methods such as the ligase chain reaction (LCR) and RNA polymerase based amplification (e.g., by transcription) methods.

The term "assemble" applies to BACs and their propensities for coming together to form contiguous stretches of DNA. A BAC "assembles" to a contig based on sequence alignment, if the BAC is sequenced, or via the alignment of its BAC fingerprint to the fingerprints of other BACs. The assemblies can be found using the Maize Genome Browser, which is publicly available on the internet.

An allele is "associated with" a trait when it is linked to it and when the presence of the allele is an indicator that the desired trait or trait form will occur in a plant comprising the allele.

A "BAC", or bacterial artificial chromosome, is a cloning vector derived from the naturally occurring F factor of *Escherichia coli*. BACs can accept large inserts of DNA sequence. In maize, a number of BACs, or bacterial artificial chromosomes, each containing a large insert of maize genomic DNA, have been assembled into contigs (overlapping contiguous genetic fragments, or "contiguous DNA").

"Backcrossing" refers to the process whereby hybrid progeny are repeatedly crossed back to one of the parents. In a backcrossing scheme, the "donor" parent refers to the parental plant with the desired gene or locus to be introgressed. The "recipient" parent (used one or more times) or "recurrent" parent (used two or more times) refers to the parental plant into which the gene or locus is being introgressed. For example, see Ragot, M. et al. (1995) Marker-assisted backcrossing: a practical example, in *Techniques et Utilisations des Marqueurs Moleculaires Les Colloques*, Vol. 72, pp. 45-56, and Openshaw et al., (1994) *Marker-assisted Selection in Backcross Breeding, Analysis of Molecular Marker Data*, pp. 41-43. The initial cross gives rise to the F1 generation; the term "BC1" then refers to the second use of the recurrent parent, "BC2" refers to the third use of the recurrent parent, and so on.

A centimorgan ("cM") is a unit of measure of recombination frequency. One cM is equal to a 1% chance that a marker at one genetic locus will be separated from a marker at a second locus due to crossing over in a single generation.

As used herein, the term "chromosomal interval" designates a contiguous linear span of genomic DNA that resides in planta on a single chromosome. The genetic elements or genes located on a single chromosomal interval are physically linked. The size of a chromosomal interval is not particularly limited. In some aspects, the genetic elements located within a single chromosomal interval are genetically linked, typically with a genetic recombination distance of, for example, less than or equal to 20 cM, or alternatively, less than or equal to 10 cM. That is, two genetic elements within a single chromosomal interval undergo recombination at a frequency of less than or equal to 20% or 10%.

A "chromosome" can also be referred to as a "linkage group".

The phrase "closely linked", in the present application, means that recombination between two linked loci occurs with a frequency of equal to or less than about 10% (i.e., are separated on a genetic map by not more than 10 cM). Put another way, the closely linked loci co-segregate at least 90% of the time. Marker loci are especially useful in the present invention when they demonstrate a significant probability of co-segregation (linkage) with a desired trait (e.g., pathogenic resistance). Closely linked loci such as a marker locus and a second locus can display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination a frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. In some cases, two different markers can have the same genetic map coordinates. In that case, the two markers are in such close proximity to each other that recombination occurs between them with such low frequency that it is undetectable.

The term "complement" refers to a nucleotide sequence that is complementary to a given nucleotide sequence, i.e. the sequences are related by the base-pairing rules.

The term "contiguous DNA" refers to overlapping contiguous genetic fragments.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand.

The term "crossed" or "cross" means the fusion of gametes via pollination to produce progeny (e.g., cells, seeds or plants). The term encompasses both sexual crosses (the pollination of one plant by another) and selfing (self-pollination, e.g., when the pollen and ovule are from the same plant). The term "crossing" refers to the act of fusing gametes via pollination to produce progeny.

A plant referred to herein as "diploid" has a paired set of chromosomes, in contrast to "haploid" which has a single set of chromosomes.

A plant referred to herein as a "doubled haploid" is developed by doubling the haploid set of chromosomes. A doubled haploid plant is considered a homozygous plant.

An "elite line" is any line that has resulted from breeding and selection for superior agronomic performance.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

An "exotic maize strain" or an "exotic maize germplasm" is a strain or germplasm derived from a maize not belonging to an available elite maize line or strain of germplasm. In the context of a cross between two maize plants or strains of germplasm, an exotic germplasm is not closely related by descent to the elite germplasm with which it is crossed. Most commonly, the exotic germplasm is not derived from any known elite line of maize, but rather is selected to introduce novel genetic elements (typically novel alleles) into a breeding program.

A "favorable allele" is the allele at a particular locus that confers, or contributes to, an agronomically desirable phenotype, e.g., enhanced resistance to northern leaf blight, and that allows the identification of plants with that agronomically desirable phenotype. A "favorable" allele of a marker is a marker allele that segregates with the favorable phenotype.

"Fragment" is intended to mean a portion of a nucleotide sequence. Fragments can be used as hybridization probes or PCR primers using methods disclosed herein.

A "genetic map" is a description of genetic linkage relationships among loci on one or more chromosomes (or chromosomes) within a given species, generally depicted in a diagrammatic or tabular form. For each genetic map, distances between loci are measured by the recombination frequencies between them, and recombinations between loci can be detected using a variety of markers. A genetic map is a product of the mapping population, types of markers used, and the polymorphic potential of each marker between different populations. The order and genetic distances between loci can differ from one genetic map to another. For example, 10 cM on the internally derived genetic map (also referred to herein as "PHB" for Pioneer Hi-Bred) is roughly equivalent to 25-30 cM on the IBM2 2005 neighbors frame map (a high resolution map available on maizeGDB). However, information can be correlated from one map to another using a general framework of common markers. One of ordinary skill in the art can use the framework of common markers to identify the positions of markers and loci of interest on each individual genetic map.

A "genetic map location" is a location on a genetic map relative to surrounding genetic markers on the same linkage group where a specified marker can be found within a given species.

"Genetic mapping" is the process of defining the linkage relationships of loci through the use of genetic markers, populations segregating for the markers, and standard genetic principles of recombination frequency.

"Genetic markers" are nucleic acids that are polymorphic in a population and where the alleles of which can be detected and distinguished by one or more analytic methods, e.g., RFLP, AFLP, isozyme, SNP, SSR, and the like. The term also refers to nucleic acid sequences complementary to the genomic sequences, such as nucleic acids used as probes. Markers corresponding to genetic polymorphisms between members of a population can be detected by methods well-established in the art. These include, e.g., PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also know for the detection of expressed sequence tags (ESTs) and SSR markers derived from EST sequences and randomly amplified polymorphic DNA (RAPD).

"Genetic recombination frequency" is the frequency of a crossing over event (recombination) between two genetic loci. Recombination frequency can be observed by following the segregation of markers and/or traits following meiosis.

"Genome" refers to the total DNA, or the entire set of genes, carried by a chromosome or chromosome set.

The term "genotype" is the genetic constitution of an individual (or group of individuals) at one or more genetic loci, as contrasted with the observable trait (the phenotype). Genotype is defined by the allele(s) of one or more known loci that the individual has inherited from its parents. The term genotype can be used to refer to an individual's genetic constitution at a single locus, at multiple loci, or, more generally, the term genotype can be used to refer to an individual's genetic make-up for all the genes in its genome.

"Germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, germplasm includes cells, seed or tissues from which new plants may be grown, or plant parts, such as leafs, stems, pollen, or cells that can be cultured into a whole plant.

A plant referred to as "haploid" has a single set (genome) of chromosomes.

A "haplotype" is the genotype of an individual at a plurality of genetic loci, i.e. a combination of alleles. Typically, the genetic loci described by a haplotype are physically and genetically linked, i.e., on the same chromosome segment. The term "haplotype" can refer to polymorphisms at a particular locus, such as a single marker locus, or polymorphisms at multiple loci along a chromosomal segment. The former can also be referred to "marker haplotypes" or "marker alleles", while the latter can be referred to as "long-range haplotypes".

The term "heterogeneity" is used to indicate that individuals within the group differ in genotype at one or more specific loci.

A "heterotic group" comprises a set of genotypes that perform well when crossed with genotypes from a different heterotic group (Hallauer et al. (1998) Corn breeding, p. 463-564. In G. F. Sprague and J. W. Dudley (ed.) *Corn and corn improvement*). Inbred lines are classified into heterotic groups, and are further subdivided into families within a heterotic group, based on several criteria such as pedigree, molecular marker-based associations, and performance in hybrid combinations (Smith et al. (1990) *Theor. Appl. Gen.* 80:833-840). The two most widely used heterotic groups in the United States are referred to as "Iowa Stiff Stalk Synthetic" (BSSS) and "Lancaster" or "Lancaster Sure Crop" (sometimes referred to as NSS, or non-Stiff Stalk).

The term "heterozygous" means a genetic condition wherein different alleles reside at corresponding loci on homologous chromosomes.

The term "homogeneity" indicates that members of a group have the same genotype at one or more specific loci.

The term "homozygous" means a genetic condition wherein identical alleles reside at corresponding loci on homologous chromosomes.

The term "hybrid" refers to the progeny obtained between the crossing of at least two genetically dissimilar parents.

"Hybridization" or "nucleic acid hybridization" refers to the pairing of complementary RNA and DNA strands as well as the pairing of complementary DNA single strands.

The term "hybridize" means to form base pairs between complementary regions of nucleic acid strands.

An "IBM genetic map" can refer to any of the following maps: IBM, IBM2, IBM2 neighbors, IBM2 FPC0507, IBM2 2004 neighbors, IBM2 2005 neighbors, IBM2 2005 neighbors frame, IBM2 2008 neighbors, IBM2 2008 neighbors frame, or the latest version on the maizeGDB website. IBM genetic maps are based on a B73×Mo17 population in which the progeny from the initial cross were random-mated for multiple generations prior to constructing recombinant inbred lines for mapping. Newer versions reflect the addition of genetic and BAC mapped loci as well as enhanced map refinement due to the incorporation of information obtained from other genetic or physical maps, cleaned data, or the use of new algorithms to produce the composite maps from individual maps.

The term "inbred" refers to a line that has been bred for genetic homogeneity.

The term "indel" refers to an insertion or deletion, wherein one line may be referred to as having an insertion relative to a second line, or the second line may be referred to as having a deletion relative to the first line.

The term "introgression" refers to the transmission of a desired allele of a genetic locus from one genetic background to another. For example, introgression of a desired allele at a specified locus can be transmitted to at least one progeny via a sexual cross between two parents of the same species, where at least one of the parents has the desired allele in its genome. Alternatively, for example, transmission of an allele can occur by recombination between two donor genomes, e.g., in a fused protoplast, where at least one of the donor protoplasts has the desired allele in its genome. The desired allele can be, e.g., a selected allele of a marker, a QTL, a transgene, or the like. In any case, offspring comprising the desired allele can be repeatedly backcrossed to a line having a desired genetic background and selected for the desired allele, to result in the allele becoming fixed in a selected genetic background. For example, the chromosome 2 locus described herein may be introgressed into a recurrent parent that is not resistant or only partially resistant to Et and/or northern leaf blight. The recurrent parent line with the introgressed gene or locus then has enhanced resistance to Et and/or northern leaf blight.

The process of "introgressing" is often referred to as "backcrossing" when the process is repeated two or more times.

A "line" or "strain" is a group of individuals of identical parentage that are generally inbred to some degree and that are generally homozygous and homogeneous at most loci (isogenic or near isogenic). A "subline" refers to an inbred subset of descendents that are genetically distinct from other similarly inbred subsets descended from the same progenitor.

As used herein, the term "linkage" is used to describe the degree with which one marker locus is associated with another marker locus or some other locus (for example, a northern leaf blight resistance locus). The linkage relationship between a molecular marker and a phenotype is given as a "probability" or "adjusted probability". Linkage can be expressed as a desired limit or range. For example, in some embodiments, any marker is linked (genetically and physically) to any other marker when the markers are separated by less than 50, 40, 30, 25, 20, or 15 map units (or cM). In some aspects, it is advantageous to define a bracketed range of linkage, for example, between 10 and 20 cM, between 10 and 30 cM, or between 10 and 40 cM. The more closely a marker is linked to a second locus, the better an indicator for the second locus that marker becomes. Thus, "closely linked loci" such as a marker locus and a second locus display an inter-locus recombination frequency of 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci display a recombination frequency of about 1% or less, e.g., about 0.75% or less, more preferably about 0.5% or less, or yet more preferably about 0.25% or less. Two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are also said to be "proximal to" each other. Since one cM is the distance between two markers that show a 1% recombination frequency, any marker is closely linked (genetically and physically) to any other marker that is in close proximity, e.g., at or less than 10 cM distant. Two closely linked markers on the same chromosome can be positioned 9, 8, 7, 6, 5, 4, 3, 2, 1, 0.75, 0.5 or 0.25 cM or less from each other.

The term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and by definition, are separated by less than 50 cM on the same chromosome.) As used herein, linkage can be between two markers, or alternatively between a marker and a phenotype. A marker locus can be "associated with" (linked to) a trait, e.g., northern leaf blight resistance. The degree of linkage of a molecular marker to a phenotypic trait is measured, e.g., as a statistical probability of co-segregation of that molecular marker with the phenotype.

Linkage disequilibrium is most commonly assessed using the measure $r^2$, which is calculated using the formula described by Hill, W. G. and Robertson, A, *Theor. Appl. Genet.* 38:226-231 (1968). When $r^2=1$, complete LD exists between the two marker loci, meaning that the markers have not been separated by recombination and have the same allele frequency. Values for $r^2$ above ⅓ indicate sufficiently strong LD to be useful for mapping (Ardlie et al., *Nature Reviews Genetics* 3:299-309 (2002)). Hence, alleles are in linkage disequilibrium when $r^2$ values between pairwise marker loci are greater than or equal to 0.33, 0.4, 0.5, 0.6, 0.7, 0.8, 0.9, or 1.0.

As used herein, "linkage equilibrium" describes a situation where two markers independently segregate, i.e., sort among progeny randomly. Markers that show linkage equilibrium are considered unlinked (whether or not they lie on the same chromosome).

A "locus" is a position on a chromosome where a gene or marker is located.

The "logarithm of odds (LOD) value" or "LOD score" (Risch, *Science* 255:803-804 (1992)) is used in interval mapping to describe the degree of linkage between two marker loci. A LOD score of three between two markers indicates that linkage is 1000 times more likely than no linkage, while a LOD score of two indicates that linkage is 100 times more likely than no linkage. LOD scores greater than or equal to two may be used to detect linkage.

"Maize" refers to a plant of the *Zeai mays* L. ssp. mays and is also known as "corn".

The term "maize plant" includes: whole maize plants, maize plant cells, maize plant protoplast, maize plant cell or maize tissue cultures from which maize plants can be regenerated, maize plant calli, and maize plant cells that are intact in maize plants or parts of maize plants, such as maize seeds, maize cobs, maize flowers, maize cotyledons, maize leaves, maize stems, maize buds, maize roots, maize root tips, and the like.

A "marker" is a nucleotide sequence or encoded product thereof (e.g., a protein) used as a point of reference. For markers to be useful at detecting recombinations, they need to detect differences, or polymorphisms, within the population being monitored. For molecular markers, this means differences at the DNA level due to polynucleotide sequence differences (e.g. SSRs, RFLPs, FLPs, and SNPs). The genomic variability can be of any origin, for example, insertions, deletions, duplications, repetitive elements, point mutations, recombination events, or the presence and sequence of transposable elements. Molecular markers can be derived from genomic or expressed nucleic acids (e.g., ESTs) and can also refer to nucleic acids used as probes or primer pairs capable of amplifying sequence fragments via the use of PCR-based methods. A large number of maize molecular markers are known in the art, and are published or available from various sources, such as the Maize GDB internet resource and the Arizona Genomics Institute internet resource run by the University of Arizona.

Markers corresponding to genetic polymorphisms between members of a population can be detected by methods well-established in the art. These include, e.g., DNA sequencing, PCR-based sequence specific amplification methods, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), or detection of amplified fragment length polymorphisms (AFLPs). Well established methods are also known for the detection of expressed sequence tags (ESTs) and SSR markers derived from EST sequences and randomly amplified polymorphic DNA (RAPD).

A "marker allele", alternatively an "allele of a marker locus", can refer to one of a plurality of polymorphic nucleotide sequences found at a marker locus in a population that is polymorphic for the marker locus.

"Marker-assisted selection" (or MAS) is a process by which phenotypes are selected based on marker genotypes.

"Marker-assisted counter-selection" is a process by which marker genotypes are used to identify plants that will not be selected, allowing them to be removed from a breeding program or planting.

A "marker haplotype" refers to a combination of alleles at a marker locus.

A "marker locus" is a specific chromosome location in the genome of a species where a specific marker can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

A "marker probe" is a nucleic acid sequence or molecule that can be used to identify the presence of a marker locus, e.g., a nucleic acid probe that is complementary to a marker locus sequence, through nucleic acid hybridization. Marker probes comprising 30 or more contiguous nucleotides of the marker locus ("all or a portion" of the marker locus sequence) may be used for nucleic acid hybridization. Alternatively, in some aspects, a marker probe refers to a probe of any type that is able to distinguish (i.e., genotype) the particular allele that is present at a marker locus.

The term "molecular marker" may be used to refer to a genetic marker, as defined above, or an encoded product thereof (e.g., a protein) used as a point of reference when identifying a linked locus. A marker can be derived from genomic nucleotide sequences or from expressed nucleotide sequences (e.g., from a spliced RNA, a cDNA, etc.), or from an encoded polypeptide. The term also refers to nucleic acid sequences complementary to or flanking the marker sequences, such as nucleic acids used as probes or primer pairs capable of amplifying the marker sequence. A "molecular marker probe" is a nucleic acid sequence or molecule that can be used to identify the presence of a marker locus, e.g., a nucleic acid probe that is complementary to a marker locus sequence. Alternatively, in some aspects, a marker probe refers to a probe of any type that is able to distinguish (i.e., genotype) the particular allele that is present at a marker locus. Nucleic acids are "complementary" when they specifically hybridize in solution, e.g., according to Watson-Crick base pairing rules. Some of the markers described herein are also referred to as hybridization markers when located on an indel region, such as the non-collinear region described herein. This is because the insertion region is, by definition, a polymorphism vis a vis a plant without the insertion. Thus, the marker need only indicate whether the indel region is present or absent. Any suitable marker detection technology may be used to identify such a hybridization marker, e.g. SNP technology is used in the examples provided herein.

An allele "negatively" correlates with a trait when it is linked to it and when presence of the allele is an indicator that a desired trait or trait form will not occur in a plant comprising the allele.

"Nucleotide sequence", "polynucleotide", "nucleic acid sequence", and "nucleic acid fragment" are used interchangeably and refer to a polymer of RNA or DNA that is single- or double-stranded, optionally containing synthetic, non-natural or altered nucleotide bases. A "nucleotide" is a monomeric unit from which DNA or RNA polymers are constructed consisting of a purine or pyrimidine base, a pentose, and a phosphoric acid group. Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "phenotype", or "phenotypic trait" or "trait" refers to one or more trait of an organism. The phenotype can be observable to the naked eye, or by any other means of evaluation known in the art, e.g., microscopy, biochemical analysis, or an electromechanical assay. In some cases, a phenotype is directly controlled by a single gene or genetic locus, i.e., a "single gene trait". In other cases, a phenotype is the result of several genes.

A "physical map" of the genome is a map showing the linear order of identifiable landmarks (including genes, markers, etc.) on chromosome DNA. However, in contrast to genetic maps, the distances between landmarks are absolute (for example, measured in base pairs or isolated and overlapping contiguous genetic fragments) and not based on genetic recombination.

A "plant" can be a whole plant, any part thereof, or a cell or tissue culture derived from a plant. Thus, the term "plant" can refer to any of: whole plants, plant components or organs (e.g., leaves, stems, roots, etc.), plant tissues, seeds, plant cells, and/or progeny of the same. A plant cell is a cell of a plant, taken from a plant, or derived through culture from a cell taken from a plant.

A "polymorphism" is a variation in the DNA that is too common to be due merely to new mutation. A polymorphism must have a frequency of at least 1% in a population. A polymorphism can be a single nucleotide polymorphism, or SNP, or an insertion/deletion polymorphism, also referred to herein as an "indel".

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the embodiments can be produced either from a nucleic acid disclosed herein, or by the use of standard molecular biology techniques. For example, a truncated protein of the embodiments can be produced by expression of a recombinant nucleic acid of the embodiments in an appropriate host cell, or alternatively by a combination of ex vivo procedures, such as protease digestion and purification.

An allele "positively" correlates with a trait when it is linked to it and when presence of the allele is an indictor that the desired trait or trait form will occur in a plant comprising the allele.

The "probability value" or "p-value" is the statistical likelihood that the particular combination of a phenotype and the presence or absence of a particular marker allele is random. Thus, the lower the probability score, the greater the likelihood that a phenotype and a particular marker will co-segregate. In some aspects, the probability score is considered "significant" or "nonsignificant". In some embodiments, a probability score of 0.05 (p=0.05, or a 5% probability) of random assortment is considered a significant indication of co-segregation. However, an acceptable probability can be any probability of less than 50% (p=0.5). For example, a significant probability can be less than 0.25, less than 0.20, less than 0.15, less than 0.1, less than 0.05, less than 0.01, or less than 0.001.

A "production marker" or "production SNP marker" is a marker that has been developed for high-throughput purposes. Production SNP markers are developed to detect specific polymorphisms and are designed for use with a variety of chemistries and platforms. The marker names used here begin with a PHM prefix to denote 'Pioneer Hybrid Marker', followed by a number that is specific to the sequence from which it was designed, followed by a "." or a "-" and then a suffix that is specific to the DNA polymorphism. A marker version can also follow (A, B, C etc) that denotes the version of the marker designed to that specific polymorphism.

The term "progeny" refers to the offspring generated from a cross.

A "progeny plant" is generated from a cross between two plants.

The term "quantitative trait locus" or "QTL" refers to a polymorphic genetic locus with at least one allele that correlates with the differential expression of a phenotypic trait in at least one genetic background, e.g., in at least one breeding population or progeny. A QTL can act through a single gene mechanism or by a polygenic mechanism.

A "reference sequence" is a defined sequence used as a basis for sequence comparison. The reference sequence is obtained by genotyping a number of lines at the locus, aligning the nucleotide sequences in a sequence alignment program (e.g. Sequencher), and then obtaining the consensus sequence of the alignment. Hence, a reference sequence identifies the polymorphisms in alleles at a locus. A reference sequence may not be a copy of an actual DNA sequence; however, it is useful for designing primers and probes for actual polymorphisms in the locus.

In "repulsion" phase linkage, the "favorable" allele at the locus of interest is physically linked with an "unfavorable" allele at the proximal marker locus, and the two "favorable" alleles are not inherited together (i.e., the two loci are "out of phase" with each other).

A "topcross test" is a progeny test derived by crossing each parent with the same tester, usually a homozygous line. The parent being tested can be an open-pollinated variety, a cross, or an inbred line.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, *CABIOS.* 5:151-153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

An "unfavorable allele" of a marker is a marker allele that segregates with the unfavorable plant phenotype, therefore providing the benefit of identifying plants that can be removed from a breeding program or planting.

The term "yield" refers to the productivity per unit area of a particular plant product of commercial value. For example, yield of maize is commonly measured in bushels of seed per acre or metric tons of seed per hectare per season. Yield is affected by both genetic and environmental factors. "Agronomics", "agronomic traits", and "agronomic performance" refer to the traits (and underlying genetic elements) of a given plant variety that contribute to yield over the course of growing season. Individual agronomic traits include emergence vigor, vegetative vigor, stress tolerance, disease resistance or tolerance, herbicide resistance, branching, flowering, seed set, seed size, seed density, standability, threshability and the like. Yield is, therefore, the final culmination of all agronomic traits.

Sequence alignments and percent identity calculations may be determined using a variety of comparison methods designed to detect homologous sequences including, but not limited to, the MEGALIGN® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp, CABIOS. 5:151 153 (1989)) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Standard recombinant DNA and molecular cloning techniques used herein are well known in the art and are described more fully in Sambrook, J., Fritsch, E. F. and Maniatis, T. *Molecular Cloning: A Laboratory Manual*; Cold Spring Harbor Laboratory Press: Cold Spring Harbor, 1989 (hereinafter "Sambrook").

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

Turning Now to the Embodiments:

Northern Leaf Blight Resistance

"Northern leaf blight" (NLB), sometimes referred to as northern corn leaf blight (NCLB), is the disease caused by the pathogen *Exserohilum turcicum*. The disease, characterized by cigar-shaped lesions on leaf tissue, can have severe effects on yield, particularly in tropical climates or during wet seasons in temperate climates.

The nucleic acids and polypeptides of the embodiments find use in methods for conferring or enhancing fungal resistance to a plant. The source of the resistance can be a naturally occurring genetic resistance locus that is introgressed via breeding into a sensitive maize population lacking the resistance locus, or alternatively, the genes conferring the resistance can be ectopically expressed as transgenes which confer resistance when expressed in the sensitive population. Accordingly, the compositions and methods disclosed herein are useful in protecting plants from fungal pathogens. "Pathogen resistance," "fungal resistance," and "disease resistance" are intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss. One of skill in the art will appreciate that the compositions and methods disclosed herein can be used with other compositions and methods available in the art for protecting plants from pathogen attack.

Hence, the methods of the embodiments can be utilized to protect plants from disease, particularly those diseases that are caused by plant fungal pathogens. As used herein, "fungal resistance" refers to enhanced resistance or tolerance to a fungal pathogen when compared to that of a wild type plant. Effects may vary from a slight increase in tolerance to the effects of the fungal pathogen (e.g., partial inhibition) to total resistance such that the plant is unaffected by the presence of the fungal pathogen. An increased level of resistance against a particular fungal pathogen, or against a wider spectrum of fungal pathogens constitutes "enhanced" or improved fungal resistance. The embodiments of the invention will enhance or improve fungal plant pathogen resistance, such that the resistance of the plant to a fungal pathogen or pathogens will increase, which in turn, will increase resistance to the disease caused by the fungal pathogen. The term "enhance" refers to improve, increase, amplify, multiply, elevate, raise, and the like. Herein, plants of the invention are described as being resistant to infection by *Helminthosporium turcicum* or having 'enhanced resistance' to infection by *Helminthosporium turcicum* as a result of the resistance locus of the invention. Accordingly, they typically exhibit increased resistance to the disease (northern leaf blight) when compared to equivalent plants that are susceptible to infection by *Helminthosporium turcicum* because they lack the resistance locus.

The identification of molecular markers and alleles of molecular markers that are associated with northern leaf blight resistance allows selection for resistance based solely on the genetic composition of the progeny. Methods for identifying and selecting maize plants with enhanced resistance to northern leaf blight through the evaluation of genetic composition (as assessed using molecular markers and their alleles) are presented herein.

In other aspects, methods for conferring or enhancing fungal resistance in a plant comprising introducing into a plant at least one expression cassette, wherein the expression cassette comprises a nucleotide sequence encoding an antifungal polypeptide of the embodiments operably linked to a promoter that drives expression in the plant, can also be performed. In these methods, the plant expresses the polypeptide, thereby conferring fungal resistance upon the plant, or improving the plant's inherent level of resistance. In particular embodiments, the gene or genes confer resistance to the fungal pathogen, *Helminthosporium turcicum*.

Expression of an antifungal polypeptide of the embodiments may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters.

Genetic Mapping—Identification of Genetic Loci Associated with Enhanced Resistance to *Helminthosporium turcicum*

It has been recognized for quite some time that specific genetic loci correlating with particular phenotypes, such as resistance to northern leaf blight, can be mapped in an organism's genome. The plant breeder can advantageously use molecular markers to identify desired individuals by detecting marker alleles that show a statistically significant probability of co-segregation with a desired phenotype, manifested as linkage disequilibrium. By identifying a molecular marker or clusters of molecular markers that co-segregate with a trait of interest, the breeder is able to rapidly select a desired phenotype by selecting for the proper molecular marker allele (a process called marker-assisted selection, or MAS). Such markers could also be used by breeders to design genotypes in silico and to practice whole genome selection.

A variety of methods well known in the art are available for detecting molecular markers or clusters of molecular markers that co-segregate with a trait of interest, such as resistance to northern leaf blight. The basic idea underlying these methods is the detection of markers, for which alternative genotypes (or alleles) have significantly different average phenotypes. Thus, one makes a comparison among marker loci of the magnitude of difference among alternative genotypes (or alleles) or the level of significance of that difference. Trait genes are inferred to be located nearest the marker(s) that have the greatest associated genotypic difference.

Two such methods used to detect trait loci of interest are: 1) Population-based association analysis and 2) Traditional linkage analysis. In a population-based association analysis, lines are obtained from pre-existing populations with multiple founders, e.g. elite breeding lines. Population-based association analyses rely on the decay of linkage disequilibrium (LD) and the idea that in an unstructured population, only correlations between genes controlling a trait of interest and markers closely linked to those genes will remain after so many generations of random mating. In reality, most pre-existing populations have population substructure. Thus, the use of a structured association approach helps to control population structure by allocating individuals to populations using data obtained from markers randomly distributed across the genome, thereby minimizing disequilibrium due to population structure within the individual populations (also called subpopulations). The phenotypic values are compared to the genotypes (alleles) at each marker locus for each line in the subpopulation. A significant marker-trait association indicates the close proximity between the marker locus and one or more genetic loci that are involved in the expression of that trait.

The same principles underlie traditional linkage analysis; however, LD is generated by creating a population from a small number of founders. The founders are selected to maximize the level of polymorphism within the constructed population, and polymorphic sites are assessed for their level of cosegregation with a given phenotype. A number of statistical methods have been used to identify significant marker-trait associations. One such method is an interval mapping approach (Lander and Botstein, *Genetics* 121:185-199 (1989), in which each of many positions along a genetic map (say at 1 cM intervals) is tested for the likelihood that a gene controlling a trait of interest is located at that position. The genotype/phenotype data are used to calculate for each test position a LOD score (log of likelihood ratio). When the LOD score exceeds a threshold value, there is significant evidence for the location of a gene controlling the trait of interest at that position on the genetic map (which will fall between two particular marker loci).

The present invention provides molecular marker loci that demonstrate statistically significant co-segregation with resistance to northern leaf blight, as determined by traditional linkage mapping techniques. Detection of these marker loci or additional linked marker loci can be used in marker-assisted maize breeding programs to produce plants with enhanced resistance to northern leaf blight or to eliminate plants that do not have enhanced resistance to northern leaf blight from breeding programs or planting.

Markers Associated with Resistance to Northern Leaf Blight

Markers associated with resistance to northern leaf blight are identified herein. The methods involve detecting the presence of one or more marker alleles associated with enhanced resistance in the germplasm of the maize plant. The maize plant can be a hybrid or inbred.

The marker locus can be selected from any of the marker loci provided herein including but not limited to: PHM2798, b0302H1, b0611N13, 2717_3, 2717_4, 108f16_2, 31004, pco642297_3, b109.m6, PHM18979, b0507L21, 2_2, 156K16, b0318i13, PHM4757, PHM13395-27, PHM4677-11, PHM3418-12, PHM15992-3, NLB5A, NLB3A, PHM4582, 9g13-3, K, 6_7, 6_8, N, R, S, U, PHM2817-26, PHM7446-6, PHM13395-16, NLB17_A, NLB17_E, NLB17_3, NLB18_A, or NLB18_E; as well as any other marker linked to these markers (linked markers can be determined from the MaizeGDB resource).

Physical Map Location

The genetic elements or genes located on a contiguous linear span of genomic DNA on a single chromosome are physically linked.

The QTL interval associated with resistance to northern leaf blight can be seen in FIG. 1 and includes BACs c0435b18, c0009g13, c0043i10, c0108f16, c0117i01, c0010k12, c0125i21, and c0064116. Any polynucleotide that assembles to the contiguous DNA between and including BACs c0435b18 and c0064116 (i.e. is 95% identical based on the Clustal V method of alignment when compared to the contiguous DNA sequence between and including BACs c0435b18 and c0064116) can house marker loci that are associated with the northern leaf blight resistance trait.

Linkage Relationships

A common measure of linkage is the frequency with which traits cosegregate. This can be expressed as a percentage of cosegregation (recombination frequency) or in centiMorgans (cM). The cM is a unit of measure of genetic recombination frequency. One cM is equal to a 1% chance that a trait at one genetic locus will be separated from a trait at another locus due to crossing over in a single generation (meaning the traits segregate together 99% of the time). Because chromosomal distance is approximately proportional to the frequency of crossing over events between traits, there is an approximate physical distance that correlates with recombination frequency.

Marker loci are themselves traits and can be assessed according to standard linkage analysis by tracking the marker loci during segregation. Thus, one cM is equal to a 1% chance that a marker locus will be separated from another locus, due to crossing over in a single generation.

The closer a marker is to a gene controlling a trait of interest, the more effective and advantageous that marker is as an indicator for the desired trait. Closely linked loci display an inter-locus cross-over frequency of about 10% or less, preferably about 9% or less, still more preferably about 8% or less, yet more preferably about 7% or less, still more preferably about 6% or less, yet more preferably about 5% or less, still more preferably about 4% or less, yet more preferably about 3% or less, and still more preferably about 2% or less. In highly preferred embodiments, the relevant loci (e.g., a marker locus and a target locus) display a recombination frequency of about 1% or less, e.g., about 0.75% or less, more preferably about 0.5% or less, or yet more preferably about 0.25% or less. Thus, the loci are about 10 cM, 9 cM, 8 cM, 7 cM, 6 cM, 5 cM, 4 cM, 3 cM, 2 cM, 1 cM, 0.75 cM, 0.5 cM or 0.25 cM or less apart. Put another way, two loci that are localized to the same chromosome, and at such a distance that recombination between the two loci occurs at a frequency of less than 10% (e.g., about 9%, 8%, 7%, 6%, 5%, 4%, 3%, 2%, 1%, 0.75%, 0.5%, 0.25%, or less) are said to be "proximal to" each other.

Although particular marker alleles can show co-segregation with the northern leaf blight resistance phenotype, it is important to note that the marker locus is not necessarily responsible for the expression of the northern leaf blight resistance phenotype. For example, it is not a requirement that the marker polynucleotide sequence be part of a gene that imparts enhanced northern leaf blight resistance (for example, be part of the gene open reading frame). The association between a specific marker allele and the enhanced northern leaf blight resistance phenotype is due to the original "coupling" linkage phase between the marker allele and the allele in the ancestral maize line from which the allele originated. Eventually, with repeated recombination, crossing over events between the marker and genetic locus can change this orientation. For this reason, the favorable marker allele may change depending on the linkage phase that exists within the resistant parent used to create segregating populations.

This does not change the fact that the marker can be used to monitor segregation of the phenotype. It only changes which marker allele is considered favorable in a given segregating population.

Markers identified herein that can be used to identify and select maize plants with enhanced resistance to northern leaf blight include: PHM2798, b0302H1, b0611N13, 2717_3, 2717_4, 108f16_2, 31004, pco642297_3, b109.m6, PHM18979, b0507L21, 2_2, 156K16, b0318i13, PHM4757, PHM13395-27, PHM4677-11, PHM3418-12, PHM15992-3, NLB5A, NLB3A, PHM4582, 9g13-3, K, 6_7, 6_8, N, R, S, U, PHM2817-26, PHM7446-6, PHM13395-16, NLB17_A, NLB17_E, NLB17_3, NLB18_A, or NLB18_E. Any marker within 50 cM of PHM2798, b0302H1, b0611N13, 2717_3, 2717_4, 108f16_2, 31004, pco642297_3, b109.m6, PHM18979, b0507L21, 2_2, 156K16, b0318i13, PHM4757, PHM13395-27, PHM4677-11, PHM3418-12, PHM15992-3, NLB5A, NLB3A, PHM4582, 9g13-3, K, 6_7, 6_8, N, R, S, U, PHM2817-26, PHM7446-6, PHM13395-16, NLB17_A, NLB17_E, NLB17_3, NLB18_A, or NLB18_E can also be used as a marker for northern leaf blight resistance.

Chromosomal Intervals

Chromosomal intervals that correlate with northern leaf blight resistance are provided. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for northern leaf blight resistance. Each interval comprises at least one QTL, and furthermore, may indeed comprise more than one QTL. Close proximity of multiple QTL in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identify the same QTL or two different QTL. Regardless, knowledge of how many QTL are in a particular interval is not necessary to make or practice the invention.

An interval on chromosome 8 containing one or more QTLs associated with northern leaf blight resistance may be defined by and includes markers:

a. PHM13395-27 and PHM4677-11;
b. PHM13395-27 and PHM3418-12;
c. 2717_4 and b0507L21;
d. 108f16_2 and pco642297_3;
e. PHM2817-26 and PHM7446-6;
f. PHM4582 and R; and
g. 6_8 and R.

Any marker located within any of these intervals finds use as a marker for northern leaf blight resistance in maize.

Chromosomal intervals can also be defined by markers that are linked to (show linkage disequilibrium with) a marker of interest, and $r^2$ is a common measure of linkage disequilibrium (LD) in the context of association studies. If the $r^2$ value of LD between any marker locus identified herein and another marker within the chromosome 8 interval (also described herein) is greater than ⅓ (Ardlie et al., *Nature Reviews Genetics* 3:299-309 (2002)), the loci are linked.

Marker Alleles and Haplotype Combinations

A marker of the invention can also be a combination of alleles at one or more marker loci, otherwise known as a haplotype. Any of the marker alleles described herein could be used alone or in combination to identify and select maize plants with enhanced northern leaf blight. This includes the CAPS markers PHM2798, b0302H1, b0611N13, 2717_3, 2717_4, 108f16_2, 31004, pco642297_3, b109.m6, PHM18979, b0507L21, 2_2, 156K16, b0318i13, PHM4757, PHM4582, 9g13-3, K, 6_7, 6_8, N, R, S, and U and their expected alleles (band sizes) shown in Tables 3 and 6 as well as the SNP marker alleles: a "G" at PHM13395-27, a "T" at PHM4677-11, an "A" at PHM3418-12, a "T" at PHM15992-3, a "C" at PHM2817-26, an "A" at PHM7446-6, and a "G" at PHM13395-16 (Tables 4 and 7).

Favorable haplotypes include but are not limited to: the PH26N haplotype at NLB17_A, the PH26N haplotype at NLB17_E, the PH26N haplotype at NLB17_3, the PH26N haplotype at NLB18_A, the PH26N haplotype at NLB18_E, the PH99N haplotype at NLB18_A, and the PH99N haplotype at NLB18_E.

The skilled artisan would expect that there might be additional polymorphic sites at marker loci in and around the chromosome 8 markers identified herein, wherein one or more polymorphic sites is in linkage disequilibrium (LD) with an allele at one or more of the polymorphic sites in the haplotype. Two particular alleles at different polymorphic sites are said to be in LD if the presence of the allele at one of the sites tends to predict the presence of the allele at the other site on the same chromosome (Stevens, *Mol. Diag.* 4:309-17 (1999)).

Marker-Assisted Selection (MAS)

Molecular markers can be used in a variety of plant breeding applications (e.g. see Staub et al. (1996) *Hortscience* 31: 729-741; Tanksley (1983) *Plant Molecular Biology Reporter.* 1: 3-8). One of the main areas of interest is to increase the efficiency of backcrossing and introgressing genes using marker-assisted selection (MAS). A molecular marker that demonstrates linkage with a locus affecting a desired phenotypic trait provides a useful tool for the selection of the trait in a plant population. This is particularly true where the phenotype is hard to assay, e.g. many disease resistance traits, or, occurs at a late stage in plant development, e.g. kernel characteristics. Since DNA marker assays are less laborious and take up less physical space than field phenotyping, much larger populations can be assayed, increasing the chances of finding a recombinant with the target segment from the donor line moved to the recipient line. The closer the linkage, the more useful the marker, as recombination is less likely to occur between the marker and the gene causing the trait, which can result in false positives. Having flanking markers decreases the chances that false positive selection will occur as a double recombination event would be needed. The ideal situation is to have a marker in the gene itself, so that recombination cannot occur between the marker and the gene. Such a marker is called a 'perfect marker'.

When a gene is introgressed by MAS, it is not only the gene that is introduced but also the flanking regions (Gepts. (2002). *Crop Sci;* 42: 1780-1790). This is referred to as "linkage drag." In the case where the donor plant is highly unrelated to the recipient plant, these flanking regions carry additional genes that may code for agronomically undesirable traits. This "linkage drag" may also result in reduced yield or other negative agronomic characteristics even after multiple cycles of backcrossing into the elite maize line. This is also sometimes referred to as "yield drag." The size of the flanking region can be decreased by additional backcrossing, although this is not always successful, as breeders do not have control over the size of the region or the recombination breakpoints (Young et al. (1998) *Genetics* 120:579-585). In classical breeding it is usually only by chance that recombinations are selected that contribute to a reduction in the size of the donor segment (Tanksley et al. (1989). *Biotechnology* 7: 257-264). Even after 20 backcrosses in backcrosses of this type, one may expect to find a sizeable piece of the donor chromosome still linked to the gene being selected. With markers however, it is possible to select those rare individuals that have experienced recombination near the gene of interest. In 150 backcross plants, there is a 95% chance that at least one plant will have experienced a crossover within 1 cM of the gene, based on a single meiosis map distance. Markers will allow unequivocal identification of those individuals. With one additional backcross of 300 plants, there would be a 95% chance of a crossover within 1 cM single meiosis map distance of the other side of the gene, generating a segment around the target gene of less than 2 cM based on a single meiosis map distance. This can be accomplished in two generations with markers, while it would have required on average 100 generations without markers (See Tanksley et al., supra). When the exact location of a gene is known, flanking markers surrounding the gene can be utilized to select for recombinations in different population sizes. For example, in smaller population sizes, recombinations may be expected further away from the gene, so more distal flanking markers would be required to detect the recombination.

The availability of integrated linkage maps of the maize genome containing increasing densities of public maize markers has facilitated maize genetic mapping and MAS. See, e.g. the IBM2 Neighbors maps, which are available online on the MaizeGDB website.

The key components to the implementation of MAS are: (i) Defining the population within which the marker-trait association will be determined, which can be a segregating population, or a random or structured population; (ii) monitoring the segregation or association of polymorphic markers relative to the trait, and determining linkage or association using statistical methods; (iii) defining a set of desirable markers based on the results of the statistical analysis, and (iv) the use and/or extrapolation of this information to the current set of breeding germplasm to enable marker-based selection decisions to be made. The markers described in this disclosure, as well as other marker types such as SSRs and FLPs, can be used in marker-assisted selection protocols.

SSRs can be defined as relatively short runs of tandemly repeated DNA with lengths of 6 bp or less (Tautz (1989) *Nucleic Acid Research* 17: 6463-6471; Wang et al. (1994) *Theoretical and Applied Genetics,* 88:1-6) Polymorphisms arise due to variation in the number of repeat units, probably caused by slippage during DNA replication (Levinson and Gutman (1987) *Mol Biol Evol* 4: 203-221). The variation in repeat length may be detected by designing PCR primers to the conserved non-repetitive flanking regions (Weber and May (1989) *Am J Hum Genet.* 44:388-396). SSRs are highly suited to mapping and MAS as they are multi-allelic, codominant, reproducible and amenable to high throughput automation (Rafalski et al. (1996) Generating and using DNA markers in plants. In: *Non-mammalian genomic analysis: a practical guide*. Academic press. pp 75-135).

Various types of SSR markers can be generated, and SSR profiles from resistant lines can be obtained by gel electrophoresis of the amplification products. Scoring of marker genotype is based on the size of the amplified fragment. An SSR service for maize is available to the public on a contractual basis by DNA Landmarks in Saint-Jean-sur-Richelieu, Quebec, Canada.

Various types of FLP markers can also be generated. Most commonly, amplification primers are used to generate fragment length polymorphisms. Such FLP markers are in many ways similar to SSR markers, except that the region amplified by the primers is not typically a highly repetitive region. Still, the amplified region, or amplicon, will have sufficient variability among germplasm, often due to insertions or deletions, such that the fragments generated by the amplification primers can be distinguished among polymorphic individuals, and such indels are known to occur frequently in maize (Bhattramakki et al. (2002). *Plant Mol Biol* 48, 539-547; Rafalski (2002b), supra).

SNP markers detect single base pair nucleotide substitutions. Of all the molecular marker types, SNPs are the most abundant, thus having the potential to provide the highest genetic map resolution (Bhattramakki et al. 2002 *Plant Molecular Biology* 48:539-547). SNPs can be assayed at an even higher level of throughput than SSRs, in a so-called 'ultra-high-throughput' fashion, as they do not require large amounts of DNA and automation of the assay may be straight-forward. SNPs also have the promise of being relatively low-cost systems. These three factors together make SNPs highly attractive for use in MAS. Several methods are available for SNP genotyping, including but not limited to, hybridization, primer extension, oligonucleotide ligation, nuclease cleavage, minisequencing and coded spheres. Such methods have been reviewed in: Gut (2001) *Hum Mutat* 17 pp. 475-492; Shi (2001) *Clin Chem* 47, pp. 164-172; Kwok (2000) *Pharmacogenomics* 1, pp. 95-100; Bhattramakki and Rafalski (2001) Discovery and application of single nucleotide polymorphism markers in plants. In: R. J. Henry, Ed, *Plant Genotyping: The DNA Fingerprinting of Plants*, CABI Publishing, Wallingford. A wide range of commercially available technologies utilize these and other methods to interrogate SNPs including Masscode™ (Qiagen), Invader® (Third Wave Technologies), SnapShot® (Applied Biosystems), Taqman® (Applied Biosystems) and Beadarrays™ (Illumina).

A number of SNPs together within a sequence, or across linked sequences, can be used to describe a haplotype for any particular genotype (Ching et al. (2002), *BMC Genet.* 3:19 pp Gupta et al. 2001, Rafalski (2002b), *Plant Science* 162:329-333). Haplotypes can be more informative than single SNPs and can be more descriptive of any particular genotype. For example, a single SNP may be allele 'T' for a specific line or variety with resistance to northern leaf blight, but the allele 'T' might also occur in the maize breeding population being utilized for recurrent parents. In this case, a haplotype, e.g. a combination of alleles at linked SNP markers, may be more informative. Once a unique haplotype has been assigned to a donor chromosomal region, that haplotype can be used in that population or any subset thereof to determine whether an individual has a particular gene. See, for example, WO2003054229. Using automated high throughput marker detection platforms known to those of ordinary skill in the art makes this process highly efficient and effective.

In addition to SSRs, FLPs and SNPs, as described above, other types of molecular markers are also widely used, including but not limited to expressed sequence tags (ESTs), SSR markers derived from EST sequences, randomly amplified polymorphic DNA (RAPD), and other nucleic acid based markers.

Isozyme profiles and linked morphological characteristics can, in some cases, also be indirectly used as markers. Even though they do not directly detect DNA differences, they are often influenced by specific genetic differences. However, markers that detect DNA variation are far more numerous and polymorphic than isozyme or morphological markers (Tanksley (1983) *Plant Molecular Biology Reporter* 1:3-8).

Sequence alignments or contigs may also be used to find sequences upstream or downstream of the specific markers listed herein. These new sequences, close to the markers described herein, are then used to discover and develop functionally equivalent markers. For example, different physical and/or genetic maps are aligned to locate equivalent markers not described within this disclosure but that are within similar regions. These maps may be within the maize species, or even across other species that have been genetically or physically aligned with maize, such as rice, wheat, barley or sorghum.

In general, MAS uses polymorphic markers that have been identified as having a significant likelihood of co-segregation with northern leaf blight resistance. Such markers are presumed to map near a gene or genes that give the plant its northern leaf blight resistance phenotype, and are considered indicators for the desired trait, or markers. Plants are tested for the presence of a desired allele in the marker, and plants containing a desired genotype at one or more loci are expected to transfer the desired genotype, along with a desired phenotype, to their progeny.

PHM2798, b0302H1, b0611N13, 2717_3, 2717_4, 108f16_2, 31004, pco642297_3, b109.m6, PHM18979, b0507L21, 2_2, 156K16, b0318i13, PHM4757, PHM13395-27, PHM4677-11, PHM3418-12, PHM15992-3, NLB5A, NLB3A, PHM4582, 9g13-3, K, 6_7, 6_8, N, R, S, U, PHM2817-26, PHM7446-6, PHM13395-16, NLB17_A, NLB17_E, NLB17_3, NLB18_A, and NLB18_E, as well as other markers genetically or physically mapped to the same chromosomal segment, may be used to select for maize plants with enhanced resistance to northern leaf blight. However, not all markers genetically and physically mapped to the same chromosomal segment may be used to select for maize plants with enhanced resistance to northern leaf blight because the marker may not be informative enough within a particular population.

The intervals presented herein find use in MAS to select plants that demonstrate enhanced resistance to northern leaf blight. Any marker that maps within the chromosome 8 interval defined by and including markers:

a. PHM13395-27 and PHM4677-11;
b. PHM13395-27 and PHM3418-12;
c. 2717_4 and b0507L21;
d. 108f16_2 and pco642297_3;
e. PHM2817-26 and PHM7446-6;
f. PHM4582 and R; and
g. 6_8 and R; for instance, can be used for this purpose.

Methods for selection can involve detecting the presence of one or more marker allele(s) linked to and associated with a marker allele or haplotype associated with enhanced resistance to northern leaf blight in a maize plant or germplasm, and then selecting the maize plant or germplasm based on the marker allele detected. The haplotype can be the PH26N haplotype at NLB17_A, the PH26N haplotype at NLB17_E, the PH26N haplotype at NLB17_3, the PH26N haplotype at NLB18_A, the PH26N haplotype at NLB18_E, the PH99N haplotype at NLB18_A, or the PH99N haplotype at NLB18_E.

Methods for MAS can also include obtaining a first maize plant that comprises within its genome a haplotype associated with enhanced resistance to northern leaf blight such as the PH26N haplotype at NLB17_A, the PH26N haplotype at NLB17_E, the PH26N haplotype at NLB17_3, the PH26N haplotype at NLB18_A, the PH26N haplotype at NLB18_E, the PH99N haplotype at NLB18_A, or the PH99N haplotype at NLB18_E; crossing the first maize plant to a second maize plant with a lower level of resistance; and genotyping the progeny for the presence of the haplotype of the first maize plant. Progeny plants possessing the haplotype of the first maize plant (i.e. the haplotype associated with enhanced resistance to northern leaf blight) can then be selected as having enhanced resistance to northern leaf blight.

Enhancing Resistance Via the Ectopic Expression of Transgenes

The embodiments of the invention also encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques (e.g. PCR amplification), or substantially free of chemical precursors or other chemicals when chemically synthesized. Optimally, an "isolated" polynucleotide is free of sequences (for example, protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof, is recombinantly produced, optimally culture medium represents less than about 30%, about 20%, about 10%, about 5%, or about 1% (by dry weight) of chemical precursors or non-protein-of-interest chemicals.

Fragments and variants of the disclosed nucleotide sequences and proteins encoded thereby are also encompassed by the embodiments. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have the ability to confer fungal resistance upon a plant. Alternatively, fragments of a nucleotide sequence that are useful as hybridization probes do not necessarily encode fragment proteins retaining biological activity. Thus, fragments of a nucleotide sequence may range from at least about 15 nucleotides, about 50 nucleotides, about 100 nucleotides, and up to the full-length nucleotide sequence encoding the polypeptides of the embodiments.

A fragment of a nucleotide sequence that encodes a biologically active portion of a polypeptide of the embodiments will encode at least about 15, about 25, about 30, about 40, or about 50 contiguous amino acids, or up to the total number of amino acids present in a full-length polypeptide of the embodiments. Fragments of a nucleotide sequence that are useful as hybridization probes or PCR primers generally need not encode a biologically active portion of a protein.

As used herein, "full-length sequence," in reference to a specified polynucleotide, means having the entire nucleic acid sequence of a native sequence. "Native sequence" is intended to mean an endogenous sequence, i.e., a non-engineered sequence found in an organism's genome.

Thus, a fragment of a nucleotide sequence of the embodiments may encode a biologically active portion of a polypeptide, or it may be a fragment that can be used as a hybridization probe or PCR primer using methods disclosed below. A biologically active portion of an antipathogenic polypeptide can be prepared by isolating a portion of one of the nucleotide sequences of the embodiments, expressing the encoded portion of the protein and assessing the ability of the encoded portion of the protein to confer or enhance fungal resistance in a plant. Nucleic acid molecules that are fragments of a nucleotide sequence of the embodiments comprise at least about 15, about 20, about 50, about 75, about 100, or about 150 nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode a protein of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Thus, for example, isolated polynucleotides that encode a polypeptide with a given percent sequence identity to the polypeptide of SEQ ID NO: 93, 95, or 97 are disclosed. Percent sequence identity between any two polypeptides can be calculated using sequence alignment programs and parameters described elsewhere herein. Where any given pair of polynucleotides of the embodiments is evaluated by comparison of the percent sequence identity shared by the two polypeptides they encode, the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the embodiments are biologically active, that is they continue to possess the desired biological activity of the native protein, that is, the ability to confer or enhance plant fungal pathogen resistance as described herein. Such variants may result, for example, from genetic polymorphism or from human manipulation. Biologically active variants of a native protein of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs and parameters described elsewhere herein. A biologically active variant of a protein of the embodiments may differ from that protein by as few as about 1-15 amino acid residues, as few as about 1-10, such as about 6-10, as few as about 5, as few as 4, 3, 2, or even 1 amino acid residue.

The proteins of the embodiments may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the embodiments include both naturally occurring sequences as well as mutant forms. Likewise, the proteins of the embodiments encompass both naturally occurring proteins as well as variations and modified forms thereof. Such variants will continue to possess the desired ability to confer or enhance plant fungal pathogen resistance. Obviously, the mutations that will be made in the DNA encoding the variant must not place the sequence out of reading frame and optimally will not create complementary regions that could produce secondary mRNA structure. See, EP Patent No. 0075444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by screening transgenic plants which have been transformed with the variant protein to ascertain the effect on the ability of the plant to resist fungal pathogenic attack.

Variant polynucleotides and proteins also encompass sequences and proteins derived from mutagenic or recombinogenic procedures, including and not limited to procedures such as DNA shuffling. One of skill in the art could envision modifications that would alter the range of pathogens to which the protein responds. With such a procedure, one or more different protein coding sequences can be manipulated to create a new protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the protein gene of the embodiments and other known protein genes to obtain a new gene coding for a protein with an improved property of interest, such as increased ability to confer or enhance plant fungal pathogen resistance. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the embodiments can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the embodiments. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species. Thus, isolated polynucleotides that encode for a protein that confers or enhances fungal plant pathogen resistance and that hybridize under stringent conditions to the sequences disclosed herein, or to variants or fragments thereof, are encompassed by the embodiments.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, and are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the embodiments. Methods for preparation of probes for hybridization and for construction of cDNA and genomic libraries are generally known in the art and are disclosed in Sambrook et al. (1989) supra.

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique and are optimally at least about 10 nucleotides in length, at least about 15 nucleotides in length, or at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) supra.

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a final wash in 0.1×SSC at 60 to 65° C. for at least 30 minutes. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) supra.

Various procedures can be used to check for the presence or absence of a particular sequence of DNA, RNA, or a protein. These include, for example, Southern blots, northern blots, western blots, and ELISA analysis. Techniques such as these are well known to those of skill in the art and many references exist which provide detailed protocols. Such references include Sambrook et al. (1989) supra, and Crowther, J. R. (2001), *The ELISA Guidebook*, Humana Press, Totowa, N.J., USA.

The following terms are used to describe the sequence relationships between two or more polynucleotides or polypeptides: (a) "reference sequence," (b) "comparison window," (c) "sequence identity," and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least about 20 contiguous nucleotides in length, and optionally can be about 30, about 40, about 50, about 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, and are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: identity and % similarity for a nucleotide sequence using Gap Weight of 50 and Length Weight of 3, and the nwsgapdna.cmp scoring matrix; % identity and similarity for an amino acid sequence using Gap Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, and no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the embodiments to polynucleotides comprising DNA. Those of ordinary skill in the art will recognize that polynucleotides can comprise ribonucleotides and combinations of ribonucleotides and deoxyribonucleotides. Such deoxyribonucleotides and ribonucleotides include both naturally occurring molecules and synthetic analogues. The polynucleotides of the embodiments also encompass all forms of sequences including, and not limited to, single-stranded forms, double-stranded forms, and the like.

Isolated polynucleotides of the embodiments can be incorporated into recombinant DNA constructs capable of introduction into and replication in a host cell. A "vector" may be such a construct that includes a replication system and sequences that are capable of transcription and translation of a polypeptide-encoding sequence in a given host cell. A number of vectors suitable for stable transfection of plant cells or for the establishment of transgenic plants have been described in, e.g., Pouwels et al., *Cloning Vectors: A Laboratory Manual,* 1985, supp. 1987; Weissbach and Weissbach, *Methods for Plant Molecular Biology*, Academic Press, 1989; and Flevin et al., *Plant Molecular Biology Manual, Kluwer Academic Publishers,* 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

The terms "recombinant construct," "expression cassette," "expression construct," "chimeric construct," "construct," "recombinant DNA construct" and "recombinant DNA fragment" are used interchangeably herein and are nucleic acid fragments. A recombinant construct comprises an artificial combination of nucleic acid fragments, including, and not limited to, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the embodiments. Screening to obtain lines displaying the desired expression level and pattern of the polynucleotides or of the resistance locus may be accomplished by amplification, Southern analysis of DNA, northern analysis of mRNA expression, immunoblotting analysis of protein expression, phenotypic analysis, and the like.

The term "recombinant DNA construct" refers to a DNA construct assembled from nucleic acid fragments obtained from different sources. The types and origins of the nucleic acid fragments may be very diverse.

In some embodiments, expression cassettes comprising a promoter operably linked to a heterologous nucleotide sequence of the embodiments are further provided. The expression cassettes of the embodiments find use in generating transformed plants, plant cells, and microorganisms and in practicing the methods for inducing plant fungal pathogen resistance disclosed herein. The expression cassette will include 5' and 3' regulatory sequences operably linked to a polynucleotide of the embodiments. "Operably linked" is intended to mean a functional linkage between two or more elements. "Regulatory sequences" refer to nucleotides located upstream (5' non-coding sequences), within, or downstream (3' non-coding sequences) of a coding sequence, and which may influence the transcription, RNA processing, stability, or translation of the associated coding sequence. Regulatory sequences may include, and are not limited to, promoters, translation leader sequences, introns, and polyadenylation recognition sequences. For example, an operable linkage between a polynucleotide of interest and a regulatory sequence (a promoter, for example) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the embodiments, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

A number of promoters can be used in the practice of the embodiments, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

It may sometimes be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the embodiments. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, and are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the polypeptides of the embodiments within a particular plant tissue. For example, a tissue-preferred promoter may be used to express a polypeptide in a plant tissue where disease resistance is particularly important, such as, for example, the roots, the stalk or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, and are not limited to, the *Prunus serotina* prunasin hydrolase gene promoter (see, e.g., International Publication No. WO 03/006651), and also those found in U.S. patent application Ser. No. 10/109,488.

Stalk-preferred promoters may be used to drive expression of a polypeptide of the embodiments. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed roIC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, and are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is a preferred endosperm-specific promoter. Glob-1 is a preferred embryo-specific promoter. For dicots, seed-specific promoters include, and are not limited to, bean β-phaseolin, napin, β-conglycinin, soybean lectin, cruciferin, and the like. For monocots, seed-specific promoters include, and are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Expression cassettes may additionally contain 5' leader sequences. Such leader sequences can act to enhance translation. Translation leaders are known in the art and include:

picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the embodiments.

In certain embodiments the nucleic acid sequences of the embodiments can be stacked with any combination of polynucleotide sequences of interest in order to create plants with a desired phenotype. This stacking may be accomplished by a combination of genes within the DNA construct, or by crossing a line containing the resistance locus with another line that comprises the combination. For example, the polynucleotides of the embodiments may be stacked with any other polynucleotides of the embodiments, or with other genes. The combinations generated can also include multiple copies of any one of the polynucleotides of interest. The polynucleotides of the embodiments can also be stacked with any other gene or combination of genes to produce plants with a variety of desired trait combinations including and not limited to traits desirable for animal feed such as high oil genes (e.g., U.S. Pat. No. 6,232,529); balanced amino acids (e.g. hordothionins (U.S. Pat. Nos. 5,990,389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005,429, filed Dec. 3, 2001)), the disclosures of which are herein incorporated by reference. The polynucleotides of the embodiments can also be stacked with traits desirable for insect, disease or herbicide resistance (e.g., *Bacillus thuringiensis* toxic proteins (U.S. Pat. Nos. 5,366,892; 5,747,450; 5,737,514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); avirulence and disease resistance genes (Jones et al. (1994) Science 266:789; Martin et al. (1993) Science 262:1432; Mindrinos et al. (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the embodiments with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including and not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant.

The methods of the embodiments may involve, and are not limited to, introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the embodiments do not depend on a particular method for introducing a sequence into a plant, only that the polynucleotide gains access to the interior of at least one cell of the plant. Methods for introducing polynucleotides into plants are known in the art including, and not limited to, stable transformation methods, transient transformation methods, and virus-mediated methods.

"Transformation" refers to the transfer of a nucleic acid fragment into the genome of a host organism, resulting in genetically stable inheritance. Host organisms containing the transformed nucleic acid fragments are referred to as "transgenic" organisms. "Host cell" refers the cell into which transformation of the recombinant DNA construct takes place and may include a yeast cell, a bacterial cell, and a plant cell. Examples of methods of plant transformation include *Agrobacterium*-mediated transformation (De Blaere et al., 1987, *Meth. Enzymol.* 143:277) and particle-accelerated or "gene gun" transformation technology (Klein et al., 1987, *Nature* (*London*) 327:70-73; U.S. Pat. No. 4,945,050), among others.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055- and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Led transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (*London*) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the embodiments provides transformed seed (also referred to as "transgenic seed") having a nucleotide construct of the embodiments, for example, an expression cassette of the embodiments, stably incorporated into their genome.

As used herein, the term "plant" can be a whole plant, any part thereof, or a cell or tissue culture derived from a plant. Thus, the term "plant" can refer to any of: whole plants, plant components or organs (including but not limited to embryos, pollen, ovules, seeds, leaves, flowers, branches, fruit, kernels, ears, cobs, husks, stalks, roots, root tips, anthers, and the like), plant tissues, plant cells, plant protoplasts, plant cell tissue cultures from which maize plant can be regenerated, plant calli, plant clumps, and plant seeds. A plant cell is a cell of a plant, either taken directly from a seed or plant, or derived through culture from a cell taken from a plant. Grain is intended to mean the mature seed produced by commercial growers for purposes other than growing or reproducing the species. Progeny, variants, and mutants of the regenerated plants are also included within the scope of the embodiments, provided that these parts comprise the introduced polynucleotides.

The embodiments of the invention may be used to confer or enhance fungal plant pathogen resistance or protect from fungal pathogen attack in plants, especially corn (*Zea mays*). It will protect different parts of the plant from attack by pathogens, including and not limited to stalks, ears, leaves, roots and tassels.

Before describing the present invention in detail, it should be understood that this invention is not limited to particular embodiments. It also should be understood that the terminology used herein is for the purpose of describing particular embodiments, and is not intended to be limiting. As used herein and in the appended claims, terms in the singular and the singular forms "a", "an" and "the", for example, include plural referents unless the content clearly dictates otherwise. Thus, for example, reference to "plant", "the plant" or "a plant" also includes a plurality of plants. Depending on the context, use of the term "plant" can also include genetically similar or identical progeny of that plant. The use of the term "a nucleic acid" optionally includes many copies of that nucleic acid molecule.

EXAMPLES

The following examples are offered to illustrate, but not to limit, the appended claims. It is understood that the examples and embodiments described herein are for illustrative purposes only and that persons skilled in the art will recognize various reagents or parameters that can be altered without departing from the spirit of the invention or the scope of the appended claims.

Example 1

Phenotyping of Northern Leaf Blight Infection

Maize plants can be evaluated for northern leaf blight (NLB) on a 1 to 9 scale, where scores of 1-3 indicate "susceptible", scores of 4-6 indicate "intermediate", and scores of 7-9 indicate "resistant". The scoring diagram in FIG. 3 can be used as a guide, with an emphasis placed on lesions above the ear. The lesions can be verified as being caused by northern leaf blight infection by checking that the lesions are cigar or boat-shaped with smooth sides and/or by sending a sample to a diagnostic lab to confirm the identity of the pathogen.

At two to four weeks after flowering, scores can be obtained from a few known susceptible lines and then compared to their historical scores. If the known susceptible lines rate at least two scores higher than their historical scores, scoring of the lines in the test set can be delayed, thereby allowing the disease to advance to a standard state of infection. The scoring period can only be extended until prior to plant senescence. Thus, if the scores are still too high after 4-5 weeks, the disease pressure is insufficient for effective scoring.

If scores from the known susceptible lines do correlate with their historical scores in the time period from 2-4 weeks after flowering until prior to plant senescence, the test lines can be scored on a plot basis using the scoring diagrams in FIG. 3 as a guide.

Example 2

Fine-Mapping of Chr8 NLB Resistance QTL from PH26N (HtBC)

Population Development and Initial QTL Mapping

An unadapted tropical proprietary maize inbred line, PH26N, was identified as a source of resistance to northern leaf blight (NLB). To facilitate the detection of one or more QTL associated with northern leaf blight resistance, a doubled haploid BC3 population of 228 lines was created, with PH26N as the donor and PH581 as the recurrent parent. Disease screening was performed as described in EXAMPLE 1, and several lines with high levels of resistance to NLB races 0 and 1, and possibly others, were identified. One doubled haploid line exhibiting NLB resistance was selected. This line was backcrossed again to PH581, and the resulting progeny were selfed. The subsequent BC4S1 population of 730 lines was then phenotyped for NLB resistance.

A QTL referred to herein as HtBC mapped to a ~2.2 cM interval between SNP markers PHM13395-27 (129.7 cM) and PHM4677-11 (131.9 cM) on chromosome 8 in bin 5 (See TABLE 4 for SNP marker information). From the BC4S1 population, 129 plants were selected, genotyped, and then phenotyped for NLB resistance via progeny testing. This led to the identification of 13 recombinants within a 0.9 cM interval defined by markers PHM13395-27 (129.7 cM) and PHM3418-12 (130.6 cM) (See TABLE 4 for SNP marker information). In an effort to obtain additional recombinants to facilitate fine-mapping efforts, 118 lines from the BC4S1 population that were heterozygous across the QTL interval were selected and selfed, and the progeny seeds were planted. From the BC4S2 population, 2477 plants were grown and genotyped, and 372 plants were selected and selfed. Seeds from the selected lines were planted in rows; the plants were genotyped; and the rows were scored for NLB resistance. As a result, 73 additional recombinants were identified within the same 0.9 cM QTL interval. In total, 86 recombinant lines were identified to be used for additional mapping.

CAPS Marker Development and Fine Mapping

The HtBC QTL interval was further delimited using the 86 recombinant lines and a set of new markers. Due to the lack of genomic sequences from either PH26N or PH581, B73 was used as a reference genome to develop the new markers. Low-copy and genic sequences within the QTL interval were identified from sequenced B73 BACs and BAC ends in the region, which were obtained from the Maize Genome Sequencing Project, and were targeted for cleaved amplified polymorphic site (CAPS) marker development. Marker primers were designed from target loci using Primer3 (Rozen and Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386), and DNA samples from parental lines PH26N and PH581 were extracted using the Gentra PUREGENE® method (Qiagen). PCR products were obtained using the set-up and parameters below (TABLES 1A and 1B) and cleaned up using the standard ExoSAP-IT® protocol (USB-Cleveland, Ohio, USA).

DNA sequencing was performed using ABI BigDye V3.1 terminator chemistry on ABI 3730 capillary sequencers (Applied Biosystems). The resulting sequences were aligned in Sequencher (GeneCodes) and analyzed for restriction-site polymorphisms stemming from SNPs or insertion/deletions (INDELs) that yield a readily distinguishable CAPS marker. DNA samples from recombinant lines were used as templates in the PCR reactions, and the PCR products were used for CAPS marker assays (TABLE 2). The resulting polymorphic fragments were scored using standard gel electrophoresis with ethidium bromide staining. In total, fourteen new CAPS markers capable of distinguishing PH581-derived genotypes versus PH26N-derived genotypes were developed (TABLE 3).

TABLE 1A

| PCR Set-Up Reaction mix | |
|---|---|
| Sample DNA | 2 ul |
| Hot StarTaq Master Mix (Qiagen) | 5 ul |
| ddH20 | 1 ul |
| F Primer (10 uM) | .5 ul |
| R Primer (10 uM) | .5 ul |
| | 10 ul total volume |

TABLE 1B

| PCR Parameters | | | |
|---|---|---|---|
| Step | Temp | Time | #Cycles |
| initial denature | 95 C. | 15 min | 1X |
| denature | 95 C. | 30 sec | |
| Anneal | 55 or 60 C.* | 60 sec | |
| extension | 72 C. | 1 min | 40X |
| final extension | 72 C. | 10 min | 1X |

TABLE 2

| CAPS Marker Assays | |
|---|---|
| PCR product | 9 ul |
| Restriction Enzyme | 1 ul |
| Buffer | 1.5 ul |
| ddH20 | 3.5 ul |
| | 15 ul total volume |

TABLE 3

CAPS Markers to Distinguish PH581-derived Genotypes From PH26N-derived Genotypes

| Marker | Target BAC | F Primer | R primer | CAPS RE | B73 Size (bp) | PH581 Fragment Size(s) | PH26N Fragment Size(s) |
|---|---|---|---|---|---|---|---|
| PHM2798 | c0520J24 | SEQ ID NO: 1 | SEQ ID NO: 2 | HaeIII | 1292 | 1292 | 474, 818 |
| b0302H1 | b0302H1 | SEQ ID NO: 3 | SEQ ID NO: 4 | AluI | 445 | 223, 145, 77 | 368, 66 |
| b0611N13 | c0043I10/ c0009G13 | SEQ ID NO: 5 | SEQ ID NO: 6 | RsaI | 584 | 299, 168, 63, 54 | 380, 180, 23 |
| 2717_3 | c0043I10/ c0009G13 | SEQ ID NO: 7 | SEQ ID NO: 8 | HhaI | 484 | 444, 40 | 260, 239 |
| 2717_4 | c0108F16/ c0043I10 | SEQ ID NO: 9 | SEQ ID NO: 10 | BstXI | 451 | 263, 188 | 451 |
| 108f16_2 | c0108F16/ c0043I10 | SEQ ID NO: 11 | SEQ ID NO: 12 | HinfI | 427 | 427 | 286, 135 |
| 31004 | c0108F16/ c0043I10 | SEQ ID NO: 13 | SEQ ID NO: 14 | AflIII | 427 | 427 | 300, 127 |
| pco642297_3 | c0117L01 | SEQ ID NO: 15 | SEQ ID NO: 16 | BsiHKAI | 550 | 318, 232 | 520 |
| b109.m6 | c0117L01/ c0108F16 | SEQ ID NO: 17 | SEQ ID NO: 18 | AluI | 401 | 182, 132, 87 | 262, 127 |
| PHM18979 | c0117L01/ c0010K12 | SEQ ID NO: 19 | SEQ ID NO: 20 | HincII | 486 | 486 | 234, 260 |
| b0507L21 | c0125I21 | SEQ ID NO: 21 | SEQ ID NO: 22 | HhaI | 434 | 374, 58, 2 | 199, 175, 58, 2 |
| 2_2 | c0064L16 | SEQ ID NO: 23 | SEQ ID NO: 24 | XbaI | 412 | 412 | 262, 150 |
| 156K16 | c0064L16 | SEQ ID NO: 25 | SEQ ID NO: 26 | Tsp509I | 562 | 562 | 290, 272 |
| b0318i13 | c0064L16 | SEQ ID NO: 27 | SEQ ID NO: 28 | BsmaI | 473 | 400, 73 | 245, 155, 73 |
| PHM4757 | c0384O20 | SEQ ID NO: 29 | SEQ ID NO: 30 | TaqI | 457 | 457 | 222, 169, 66 |

Fine mapping using the CAPS markers (described in TABLE 3) and the 86 recombinant lines further defined the HtBC QTL interval to a region defined by and including markers 2717_4 and b0507L21. The interval spans five B73 BACs (c0043i10, c0108f16, c0117101, c0010k12, and c0125i21; FIG. 1) and represents ~552 kb in maize genomic sequence (Maize Genome Sequencing Project).

An additional set of recombinant lines was generated from the BC4S1 and BC4S2 lines described above. Lines heterozygous across the HtBC QTL interval were selected, selfed, and bulk harvested, and the progeny seed was planted. The plants were genotyped with two available production SNP markers, PHM13395-27 (129.7 cM) and PHM15992-3 (128.8 cM) to identify heterozygous recombinants across the region (See TABLE 4 for SNP marker information). Three hundred and ninety recombinants were identified and genotyped with the same CAPS markers previously used to delimit the QTL to a five BAC interval (2717_4 and 507L21), and 34 recombinants spanned the narrowed QTL interval.

Fourteen recombinants were selected to be assayed for NLB resistance in the greenhouse via progeny testing. For the greenhouse assay, *Exserohilum turcicum* was grown on artificial media to produce spores for artificial inoculation. Spores were collected and suspended in sterile water, and the suspension was diluted to $1\times10^4$ spores/ml. One hundred micro liters (μl) of the spore suspension was used to inoculate each greenhouse-grown seedling at V3 stage. Twenty four hours after the first inoculation, the plants were re-inoculated and then placed in a humid chamber overnight at room temperature. Plants were taken out of the humid chamber and placed on a greenhouse bench for the duration of the test, and plants were regularly watered and fertilized as needed. Scoring for disease incidence, as resistant (0) or susceptible (1), was done at 9 and 12 days after the first inoculation for each plant.

Based on the recombination data obtained from the fourteen recombinants (using the greenhouse assay), the HtBC QTL interval was further delimited to an interval spanning two BACs (c0108f16, c0117101; FIG. 1), which is defined by and includes markers 108f16_2 and pco642297_3 and represents ~217 kb in maize genomic sequence (Maize Genome Sequencing Project).

TABLE 4

HtBC SNP Markers

| Markers | F Primer | R primer | SNPS |
|---|---|---|---|
| PHM13395-27 | SEQ ID NO: 63 | SEQ ID NO: 64 | pos 308 of SEQ ID NO: 81 PH581 = A, PH26N = G |
| PHM4677-11 | SEQ ID NO: 65 | SEQ ID NO: 66 | pos 281 of SEQ ID NO: 82 PH581 = G, PH26N = T |
| PHM3418-12 | SEQ ID NO: 61 | SEQ ID NO: 62 | pos 392 of SEQ ID NO: 83 PH581 = C, PH26N = A |
| PHM15992-3 | SEQ ID NO: 67 | SEQ ID NO: 68 | pos 518 of SEQ ID NO: 84 PH581 = G, PH26N = T |

PH26N BAC Library Construction, Screening, and Assembly

In an effort to characterize the gene content of the genomic region within the HtBC QTL interval, a BAC library was constructed from PH26N. Nuclei were isolated from about 200 PH26N etiolated seedlings embedded in low-melting-point agarose and lysed in gel. Embedded high-molecular-weight DNA was partially digested with Hind III, and 150-300 kb fragments fractionated twice by Clamped Homogeneous Electric Field (CHEF) agarose gel electrophoresis. Micro-eluted fragments were ligated into vector pCCBAC1 (Epicentre) following manufacturer's conditions, and electroporated into Epi300 cells. More than 56,000 clones (4×) were individually arrayed, gridded in nylon membranes, and screened by nonradioactive hybridization to two probes adjacent to the left flanking marker 108f16_2, NLB5A and NLB3A (TABLE 5). Two positive BACs were identified from this screening (cbacPH26Nh.pk136.o20, cbacPH26N.pk016.p6) and confirmed by PCR with primers from the probes and from flanking markers. These BACs were sequenced and assembled together, which resulted in a 215 kb sequence containing.

TABLE 5

Primer and Probe Information for NLB5A and NLB3A

| | F Primer | R primer | Probe |
|---|---|---|---|
| NLB5A | SEQ ID NO: 31 | SEQ ID NO: 32 | SEQ ID NO: 33 |
| NLB3A | SEQ ID NO: 34 | SEQ ID NO: 35 | SEQ ID NO: 36 |

HtBC Candidate Genes

The narrowed HtBC QTL interval contains two predicted tandem protein kinase (PK)-like candidate genes that are referred to herein as NLB17 and NLB18 (FIG. 2). The cDNA sequences of these candidate genes are represented by SEQ ID NO:92 and SEQ ID NO:96, respectively, and the amino acid sequences of the predicted encoded polypeptides are represented by SEQ ID NOs:93 and 97.

Example 3

Fine-Mappinq of Chr8 NLB Resistance QTL from PH99N (Htn1)

Initial QTL Mapping

Line PH99N was identified as a source of resistance to northern leaf blight (NLB). In an effort to identify one or more QTL associated with NLB resistance in PH99N, BC4 and BC4S1 populations were developed using PH581 as the recurrent (susceptible) parent. From these populations, 505 and 583 plants, respectively, were genotyped with SNP markers and assayed for NLB resistance using single-plant analysis. A QTL referred to herein as Htn1 was mapped to a 0.6 cM interval between SNP markers PHM2817-26 (128.8) and PHM7446-6 (129.4) (TABLE 7) on chromosome 8 in bin 5. From these experiments, 100 heterozygous recombinant lines were selected for progeny testing assays (see EXAMPLE 2 for greenhouse assay methods) for NLB resistance in the greenhouse.

CAPS Marker Development and Fine-Mapping

Fine-mapping of Htn1 was initiated using the 100 heterozygous recombinants described above. Low-copy and genic sequences within the QTL interval, from the reference genome B73, were targeted for CAPS marker development (see EXAMPLE 2 for methods). Ten new CAPS markers that distinguish PH99N-derived genotypes from PH581-derived genotypes were developed (TABLE 6) and were used to further characterize the genotypes of the recombinants.

TABLE 6

CAPS Markers to Distinguish PH581-derived Genotypes From PH99N-derived Genotypes

| CAPS Marker | Target BAC | F Primer | R primer | CAPS RE | B73 Size (bp) | PH581 Fragment Size(s) | PH99N Fragment Size(s) |
|---|---|---|---|---|---|---|---|
| PHM4582 | c0435b18 | SEQ ID NO: 41 | SEQ ID NO: 42 | AvaII | 595 | 5995 | 363, 232 |
| 9g13-3 | c0009G13 | SEQ ID NO: 43 | SEQ ID NO: 44 | AluI | 500 | 484, 16 | 357, 127, 16 |
| K | c0009G13/ c0043I10 | SEQ ID NO: 45 | SEQ ID NO: 46 | MaeIII | 402 | 278, 124 | 211, 124, 67 |
| 6_7 | c0043I10 | SEQ ID NO: 47 | SEQ ID NO: 48 | MspI | 524 | 446, 57, 21 | 273, 173, 57, 21 |
| 6_8 | c0043i10/ c0108f16 | SEQ ID NO: 49 | SEQ ID NO: 50 | MspI | 554 | 312, 238, 4 | 550, 4 |
| N | c0108F16/ c0117L01 | SEQ ID NO: 51 | SEQ ID NO: 52 | BsrDI | 491 | 491 | 248, 243 |
| R | c0117L01 | SEQ ID NO: 53 | SEQ ID NO: 54 | BbsI | 465 | 214, 146, 105 | 364, 105 |
| S | c0125I21 | SEQ ID NO: 55 | SEQ ID NO: 56 | StuI | 477 | 477 | 383, 94 |
| U | c0064L16 | SEQ ID NO: 57 | SEQ ID NO: 58 | XmnI | 472 | 250, 222 | 472 |
| PHM4757 | c0384O20 | SEQ ID NO: 29 | SEQ ID NO: 30 | BsmaI | 457 | 441, 11, 5 | 274, 167, 11, 5 |

Recombination mapping delimited the QTL interval to the region defined by and including markers PHM4582 and R. This region spans five B73 BACs (c0435b18, c0009g13, c0043i10, c0108f16, c0117L01; FIG. 1) and represents ~475 kb in maize genomic sequence (Maize Genome Sequencing Project).

In order to obtain additional recombinants, BC4 lines that were heterozygous across the new QTL interval were selected, selfed, and bulk harvested. The resulting 4876 segregating BCSI lines were kernel chipped and genotyped with two available production SNP markers in the vicinity of the Htn1 QTL, PHM13395-16 (129.6 cM) and PHM3418-12 (130.6 cM) (See TABLE 7). From the BCS1 population, 932 recombinant lines were selected and selfed, and progeny seeds from 761 of the selected recombinant lines were planted and genotyped with the same CAPS markers previously used to delimit Htn1 to the five BAC interval, PHM4582 and R. Ten additional recombinants were identified and were subsequently scored for NLB resistance via progeny tests in greenhouse assays (as described in EXAMPLE 2) and then genotyped with the four remaining CAPS markers in the Htn1 interval. The Htn1 QTL interval was further refined to the interval defined by and including markers 6_8 and R, which includes two BACs (c0108f16, c0117L01; FIG. 1) and represents ~224 kb in maize genomic sequence (Maize Genome Sequencing Project).

TABLE 7

Htn1 SNP Markers

| Markers | F Primer | R primer | SNPS |
|---|---|---|---|
| PHM2817-26 | SEQ ID NO: 37 | SEQ ID NO: 38 | pos 316 in SEQ ID NO: 85 PH581 = T, PH99N = C |
| PHM7446-6 | SEQ ID NO: 39 | SEQ ID NO: 40 | pos 231 in SEQ ID NO: 86 PH581 = G, PH99N = A |
| PHM13395-16 | SEQ ID NO: 59 | SEQ ID NO: 60 | pos 183 in SEQ ID NO: 81 PH581 = A, PH99N = G |
| PHM3418-12 | SEQ ID NO: 61 | SEQ ID NO: 62 | pos 392 in SEQ ID NO: 83 PH581 = C, PH99N = A |

Htn1 Candidate Genes

The Htn1 QTL interval spans 82.9 kb based on the genomic sequence derived from the PH26N BAC sequence assembly (EXAMPLE 2; FIG. 2). The HtBC QTL coincides with the Htn1 QTL interval. Consequently, the two predicted tandem protein kinase (PK)-like genes (NLB17, NLB18) that were identified as candidate genes for HtBC are also likely candidate genes for Htn1, if present in this region of the Htn1 genome. However, it appears that Htn1 lacks NLB17. SEQ ID NO:94 and 95 represent the nucleotide sequence of the NLB18 cDNA in PH99N and the amino acid sequence of the encoded protein product, respectively.

Example 4

Haplotype Analysis of Chr8 NLB HtBC and Htn1 Candidate Genes

Haplotypes can be more informative than single SNPs and can be more descriptive of any particular genotype. In addition, once a unique haplotype has been assigned to a donor chromosomal region, that haplotype can be used in that population or any subset thereof to determine whether an individual has a particular gene and/or allele. (See, for example, WO2003054229).

Haplotype analysis was performed via the re-sequencing of the two protein kinase (PK)-like QTL candidate genes for HtBC and Htn1 (NLB17,NLB18) using a panel of maize lines phenotyped for northern leaf blight. The highly conserved nature of the kinase catalytic domain of the two tandem PK-like candidate genes posed a challenge for PCR primer design. Moreover, a lack of ESTs for these two genes made it difficult to determine their exact structure. Therefore, to facilitate the design of specific primers capable of both distinguishing these two loci and amplifying from a diverse panel of maize lines, a multiple sequence alignment was performed using ClustalW from genomic sequences of B73 and PH26N spanning the PK domain of both NLB17 and NLB18. From this alignment, three primers were developed to specifically amplify portions of NLB17, and two were designed for NLB18 (TABLE 8). Short sequencing tails were added to these primers to facilitate sequencing. PCR and sequencing were performed as previously described (TABLES 1A and 1B; EXAMPLE 1).

TABLE 8

Markers Designed for NLB17 and NLB18 Candidate Genes

| Marker | BAC | Target | F Primer* | R primer^ |
|---|---|---|---|---|
| NLB17_A | c0108f16/ c0117L01 | putative protein kinase #1 | SEQ ID NO: 69 | SEQ ID NO: 70 |
| NLB17_E | c0108f16/ c0117L01 | putative protein kinase #1 | SEQ ID NO: 71 | SEQ ID NO: 72 |
| NLB17_3 | c0108f16/ c0117L01 | putative protein kinase #1 | SEQ ID NO: 73 | SEQ ID NO: 74 |
| NLB18_A | c0117L01 | putative protein kinase #2 | SEQ ID NO: 75 | SEQ ID NO: 76 |
| NLB18_E | c0117L01 | putative protein kinase #2 | SEQ ID NO: 77 | SEQ ID NO: 78 |

*sequencing tail added to F primers: SEQ ID NO: 79

^sequencing tail added to R primers: SEQ ID NO: 80

The markers were used to re-sequence the corresponding five amplicons from a panel of 190 maize inbreds, including PH26N and PH99N. SNPs and INDELs were used to classify the inbreds in the panel into various haplotype groups (TABLE 9).

TABLE 9

NLB17 and NLB18 Amplicon Information

| Amplicon | SNPs | INDELs | Haplotypes | Consensus Length (bp)* | Depth (out of 190 lines) |
|---|---|---|---|---|---|
| NLB17_A (SEQ ID NO: 87) | 7 | 4 | 5 | 707 | 86 lines |
| NLB17_E (SEQ ID NO: 88) | 10 | 2 | 6 | 961 | 104 lines |
| NLB17_3 (SEQ ID NO: 89) | 61 | 7 | 10 | 539 | 113 lines |
| NLB18_A (SEQ ID NO: 90) | 27 | 29 | 9 | 784 | 100 lines |
| NLB18_E (SEQ ID NO: 91) | 19 | 6 | 12 | 624 | 171 lines (poss. duplication) |

*Consensus length may contain a few bases from sequencing tails.

The amplification success rate for the various primers ranged from 45-90%. This lack of amplification may be an additional indicator of diversity in the candidate gene region amongst the panel of inbreds. Given the high degree of gene non-colinearity among maize lines, it is possible that these genes are not present in the tested lines or that the genes were too different, with SNPs in the priming site, causing the primers to not anneal properly. Interestingly, none of the three primers from NLB17 yielded a product in PH99N, which suggests that this gene is not present and thus, not a candidate gene for the Htn1 NLB resistance QTL. TABLE 10 shows the haplotype information for PH26N at each of the NLB17 markers. TABLE 11 shows the haplotype information for both PH26N and PH99N at each of the NLB18 markers.

TABLE 10

NLB17 Haplotype Information for PH26N

| Position in SEQ ID NO: 89 (NLB17_3) | PH26N | Position in SEQ ID NO: 87 (NLB17_A) | PH26N | Position in SEQ ID NO: 88 (NLB17_E) | PH26N |
|---|---|---|---|---|---|
| 38 | C | 112 | G | 52 | * |
| 40 | T | 143 | A | 75 | ****** |
| 43 | C | 201 | C | 209 | C |
| 48 | T | 230 | G | 295 | C |
| 60 | C | 232 | T | 527 | C |
| 61 | A | 233 | A | 543 | A |
| 63 | T | 281 | A | 554 | A |
| 67 | C | 341 | A | 569 | A |
| 71 | T | 389 | T | 617 | T |
| 72 | A | 472 | * | 674 | C |
| 73 | A | 473 | A | 739 | T |
| 74 | * | | | 800 | A |
| 82 | C | | | | |
| 83 | A | | | | |
| 91 | C | | | | |
| 92 | T | | | | |
| 102 | G | | | | |
| 104 | T | | | | |
| 107 | G | | | | |
| 109 | C | | | | |
| 110 | C | | | | |
| 111 | T | | | | |
| 114 | A | | | | |
| 136 | A | | | | |
| 138 | T | | | | |
| 157 | A | | | | |
| 158 | G | | | | |
| 169 | A | | | | |
| 173 | AAATACACT | | | | |
| 185 | G | | | | |
| 187 | A | | | | |
| 190 | A | | | | |
| 200 | C | | | | |
| 207 | T | | | | |
| 209 | A | | | | |
| 216 | C | | | | |
| 226 | A | | | | |

TABLE 10-continued

| NLB17 Haplotype Information for PH26N | | | | | |
|---|---|---|---|---|---|
| Position in SEQ ID NO: 89 (NLB17_3) | PH26N | Position in SEQ ID NO: 87 (NLB17_A) | PH26N | Position in SEQ ID NO: 88 (NLB17_E) | PH26N |
| 230 | AG | | | | |
| 249 | A | | | | |
| 255 | A | | | | |
| 263 | A | | | | |
| 266 | T | | | | |
| 273 | C | | | | |
| 274 | T | | | | |
| 275 | C | | | | |
| 287 | A | | | | |
| 291 | A | | | | |
| 295 | G | | | | |
| 312 | A | | | | |
| 318 | C | | | | |
| 320 | C | | | | |
| 325 | A | | | | |
| 328 | C | | | | |
| 333 | G | | | | |
| 340 | G | | | | |
| 354 | C | | | | |
| 367 | T | | | | |
| 368 | A | | | | |
| 369 | A | | | | |
| 373 | G | | | | |
| 380 | G | | | | |
| 389 | G | | | | |
| 392 | C | | | | |
| 396 | A | | | | |
| 407 | C | | | | |
| 424 | G | | | | |
| 434 | T | | | | |
| 435 | G | | | | |

TABLE 11

| NLB18 Haplotype Information for PH26N and PH99N | | | | | |
|---|---|---|---|---|---|
| Position in SEQ ID NO: 90 (NLB18_A) | PH26N | PH99N | Position in SEQ ID NO: 91 (NLB18_E) | PH26N | PH99N |
| 45 | A | * | 38 | T | T |
| 61 | A | C | 46 | T | G |
| 77 | T | T | 81 | * | * |
| 82 | A | G | 82 | * | * |
| 88 | C | C | 83 | * | * |
| 113 | A | A | 94 | CGCTTG | ****** |
| 116 | C | C | 104 | C | C |
| 117 | C | G | 107 | T | G |
| 131 | T | C | 170 | G | T |
| 143 | T | T | 173 | T | T |
| 147 | * | A | 174 | G | A |
| 156 | T | T | 234 | A | G |
| 201 | * | * | 263 | A | A |
| 202 | * | * | 277 | G | G |
| 208 | C | C | 299 | A | A |
| 237 | G | G | 368 | C | C |
| 242 | A | A | 399 | * | * |
| 243 | T | T | 400 | * | * |
| 250 | T | T | 406 | T | T |
| 267 | G | A | 421 | C | C |
| 278 | T | T | 431 | G | G |
| 289 | A | A | 435 | G | G |
| 301 | C | C | 464 | A | A |
| 302 | T | T | 492 | G | G |
| 303 | G | G | 535 | A | A |
| 345 | * | * | | | |
| 349 | * | * | | | |
| 350 | * | * | | | |
| 354 | A | A | | | |
| 355 | A | T | | | |
| 360 | C | G | | | |
| 362 | * | * | | | |
| 364 | * | * | | | |
| 365 | * | * | | | |
| 389 | T | C | | | |
| 395 | * | * | | | |
| 396 | * | * | | | |

TABLE 11-continued

| NLB18 Haplotype Information for PH26N and PH99N | | | | | |
|---|---|---|---|---|---|
| Position in SEQ ID NO: 90 (NLB18_A) | PH26N | PH99N | Position in SEQ ID NO: 91 (NLB18_E) | PH26N | PH99N |
| 397 | * | * | | | |
| 399 | C | C | | | |
| 437 | A | A | | | |
| 445 | T | T | | | |
| 458 | A | T | | | |
| 491 | C | C | | | |
| 492 | A | A | | | |
| 493 | A | A | | | |
| 494 | A | A | | | |
| 495 | A | A | | | |
| 496 | A | A | | | |
| 497 | A | A | | | |
| 498 | A | A | | | |
| 499 | A | A | | | |
| 500 | * | A | | | |
| 519 | GTAACCA | ******* | | | |
| 557 | T | T | | | |
| 571 | ** | ** | | | |
| 588 | CTG | CTG | | | |

Example 5

Use of NLB17 and NLB18 as Transgenes to Create Resistant Corn Plants

The NLB17 and NLB18 genes can be expressed as transgenes as well, either alone or in combination, allowing modulation of their expression in different circumstances. The following examples show how the NLB17 and/or NLB18 genes could be expressed in different ways to combat different diseases or protect different portions of the plant, or simply to move the NLB17 and/or NLB18 genes into different corn lines as transgenes.

Example 5a

In this example, a candidate gene is expressed using its own promoter.

In order to transform the complete gene, including the promoter and protein encoding regions, DNA fragments containing the complete coding region and approximately 2 kb upstream region are amplified by PCR using the BAC clone as template DNA. To enable cloning using the Gateway® Technology (Invitrogen, Carlsbad, USA), attB sites are incorporated into the PCR primers, and the amplified product is cloned into pDONR221 vector by Gateway® BP recombination reaction. The resulting fragment, flanked by attL sites, is moved by the Gateway® LR recombination reaction into a binary vector. The construct DNA is then used for corn transformation as described in Example 6.

Example 5b

In order to express a candidate gene throughout the plant at a low level, the coding region of the gene and its terminators are placed behind the promoters of either a rice actin gene (U.S. Pat. No. 5,641,876 and No. 5,684,239) or the F3.7 gene (U.S. Pat. No. 5,850,018). To enable cloning using the Gateway® Technology (Invitrogen, Carlsbad, USA), attB sites are incorporated into PCR primers that are used to amplify the candidate gene starting 35 bp upstream from its initiation codon. A NotI site is added to the attB1 primer. The amplified product is cloned into pDONR221 vector by Gateway® BP recombination reaction (Invitrogen, Carlsbad, USA). After cloning, the resulting gene is flanked by attL sites and has a unique NotI site at 35 bp upstream the initiation codon. Thereafter, promoter fragments are PCR amplified using primers that contain NotI sites. Each promoter is fused to the NotI site of the candidate gene. In the final step, the chimeric gene construct is moved by Gateway® LR recombination reaction (Invitrogen, Carlsbad, USA) into the binary vector PHP20622. This is used for corn transformation as described in Example 6.

Example 5c

In order to express the candidate gene(s) throughout the plant at a high level, the coding region of the gene and its terminator are placed behind the promoter, 5' untranslated region and an intron of a maize ubiquitin gene (Christensen et al. (1989) *Plant Mol. Biol.* 12:619-632; Christensen et al. (1992) *Plant Mol. Biol.* 18:675-689). To enable cloning using the Gateway® Technology (Invitrogen, Carlsbad, USA), attB sites are incorporated into PCR primers that are used to amplify the candidate gene starting at 142 bp upstream of the initiation codon. The amplified product is cloned into pDONR221 (Invitrogen, Carlsbad, USA) using a Gateway® BP recombination reaction (Invitrogen, Carlsbad, USA). After cloning, the resulting gene is flanked by attL sites. In the final step, the clone is moved by Gateway LR recombination reaction (Invitrogen, Carlsbad, USA) into a vector which contained the maize ubiquitin promoter, 5' untranslated region and first intron of the ubiquitin gene as described by Christensen et al. (supra) followed by Gateway® ATTR1 and R2 sites for insertion of the candidate gene, behind the ubiquitin expression cassette. The vector also contains a marker gene suitable for corn transformation, so the resulting plasmid, carrying the chimeric gene (maize ubiquitin promoter-ubiquitin 5' untranslated region-ubiquitin intron 1-candidate gene), is suitable for corn transformation as described in Example 6.

Example 5d

In order to express the candidate gene(s) at a root-preferred, low level of expression, the coding region of the gene and its terminator are placed behind a root preferred promoter such as but not limited to, maize NAS2 promoter, the maize Cyclo promoter (US 2006/0156439, published Jul. 13, 2006), the maize ROOTMET2 promoter (WO05063998, published Jul. 14, 2005), the CR1BIO promoter (WO06055487, published May 26, 2006), the CRWAQ81 (WO05035770, published Apr. 21, 2005) and the maize ZRP2.47 promoter (NCBI accession number: U38790; GI No. 1063664). The fragment described in Example 5b containing the coding region of the candidate gene flanked by attL sites and containing a unique NotI site 35 bp upstream of the initiation codon is used to enable cloning using the Gateway® Technology (Invitrogen, Carlsbad, USA). Promoter fragment is PCR amplified using primers that contain NotI sites. Each promoter is fused to the NotI site of the candidate gene. In the final step, the chimeric gene construct is moved by Gateway® LR recombination reaction (Invitrogen, Carlsbad, USA) into the binary vector PHP20622. This is used for corn transformation as described in Example 6.

Example 6

*Agrobacterium*-Mediated Transformation of Maize and Regeneration of Transgenic Plants The recombinant DNA constructs described in Example 5a-5d can be used to prepare transgenic maize plants as follows.

Maize is transformed with selected polynucleotide constructs described in Examples 5a and 5c using the method of Zhao (U.S. Pat. No. 5,981,840, and PCT patent publication WO98/32326). Briefly, immature embryos are isolated from maize and the embryos contacted with a suspension of *Agrobacterium*, where the bacteria are capable of transferring the polynucleotide construct to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent, and growing transformed callus is recovered (step 4: the selection step). The callus is then regenerated into plants (step 5: the regeneration step), and calli grown on selective medium were cultured on solid medium to regenerate the plants.

Example 7

Transgenic Plant Evaluation

Transgenic plants can be made as described in Example 6 using the constructs described in Examples 5a to 5d. They can be evaluated for northern leaf blight resistance using the protocol described in Example 1.

What is claimed:

1. A method of selecting a maize plant with enhanced resistance to northern leaf blight, the method comprising:

a. isolating nucleic acids from a maize plant;

b. analyzing the isolated nucleic acids for the presence of a QTL allele associated with the enhanced resistance to northern leaf blight, wherein the presence of said QTL allele is determined by detecting in the maize plant at least one marker allele that is linked to and associated with a haplotype selected from the group consisting of:

i. a "G" at PHM13395-27 and an "A" at PHM3418-12; and ii. a "C" at PHM2817-26 and an "A" at PHM7446-6; and wherein said at least one marker allele is within 10 cM of the haplotype; and b. selecting said maize plant that has the at least one marker allele.

2. The method of claim 1, wherein the at least one marker allele is within 5 cM of the haplotype.

3. The method of claim 1, wherein the at least one marker allele is within 1 cM of the haplotype.

4. A method of selecting a maize plant with enhanced resistance to northern leaf blight, the method comprising:

a. isolating nucleic acids from a maize plant;

b. analyzing the isolated nucleic acids for the presence of a QTL allele associated with the enhanced resistance to northern leaf blight, wherein the presence of said QTL allele is determined by detecting in the maize plant a haplotype selected from the group consisting of:

i. a “G” at PHM13395-27 and an “A” at PHM3418-12; and ii. a “C” at PHM2817-26 and an “A” at PHM7446-6; and b. selecting said maize plant that has said haplotype.

* * * * *

SEQUENCE LISTING

```
<160> NUMBER OF SEQ ID NOS: 97

<210> SEQ ID NO 1
<211> LENGTH: 20
<212> TYPE: DNA
<213> ORGANISM: artificial
<220> FEATURE:
<223> OTHER INFORMATION: PHM2798 F Primer

<400> SEQUENCE: 1

gactcggtta agaagaggga                                                  20


<210> SEQ ID NO 2
<211> LENGTH: 20
<212> TYPE: DNA
<213> ORGANISM: artificial
<220> FEATURE:
<223> OTHER INFORMATION: PHM2798 R Primer

<400> SEQUENCE: 2

tcaagaatcc taggtggcag                                                  20


<210> SEQ ID NO 3
<211> LENGTH: 20
<212> TYPE: DNA
<213> ORGANISM: artificial
<220> FEATURE:
<223> OTHER INFORMATION: b0302H1 F primer

<400> SEQUENCE: 3

tatgggagaa gatggcaacc                                                  20


<210> SEQ ID NO 4
<211> LENGTH: 20
<212> TYPE: DNA
<213> ORGANISM: artificial
```

<220> FEATURE:
<223> OTHER INFORMATION: b0302H1 R Primer

<400> SEQUENCE: 4
cccacttaag ggttgtgtcc 20

<210> SEQ ID NO 5
<211> LENGTH: 20
<212> TYPE: DNA
<213> ORGANISM: artificial
<220> FEATURE:
<223> OTHER INFORMATION: b0611n13 F Primer

<400> SEQUENCE: 5
ttgttgggct tcgtatctcc 20

<210> SEQ ID NO 6
<211> LENGTH: 19
<212> TYPE: DNA
<213> ORGANISM: artificial
<220> FEATURE:
<223> OTHER INFORMATION: b0611n13 R Primer

<400> SEQUENCE: 6
catgcctcaa attgcaagg 19

<210> SEQ ID NO 7
<211> LENGTH: 20
<212> TYPE: DNA
<213> ORGANISM: artificial
<220> FEATURE:
<223> OTHER INFORMATION: 2717_3 F Primer

<400> SEQUENCE: 7
ggcgactaca gggttagagc 20

<210> SEQ ID NO 8
<211> LENGTH: 20
<212> TYPE: DNA
<213> ORGANISM: artificial
<220> FEATURE:
<223> OTHER INFORMATION: 2717_3 R Primer

<400> SEQUENCE: 8
ggccttccat atcagtttcg 20

<210> SEQ ID NO 9
<211> LENGTH: 20
<212> TYPE: DNA
<213> ORGANISM: artificial
<220> FEATURE:
<223> OTHER INFORMATION: 2717_4 F Primer

<400> SEQUENCE: 9
actcctgctc ctcttgttcg 20

<210> SEQ ID NO 10
<211> LENGTH: 20
<212> TYPE: DNA
<213> ORGANISM: artificial
<220> FEATURE:
<223> OTHER INFORMATION: 2717_4 R Primer

<400> SEQUENCE: 10
cgctacccgt tctatcttgc 20

<210> SEQ ID NO 11
<211> LENGTH: 21
<212> TYPE: DNA
<213> ORGANISM: artificial
<220> FEATURE:
<223> OTHER INFORMATION: 108f16_2 F Primer

<400> SEQUENCE: 11
gagtgggtgt cgtagttcag c 21

<210> SEQ ID NO 12
<211> LENGTH: 20
<212> TYPE: DNA
<213> ORGANISM: artificial
<220> FEATURE:
<223> OTHER INFORMATION: 108f16_2 R Primer

<400> SEQUENCE: 12
tcgactacaa gacgcgtacc 20

<210> SEQ ID NO 13
<211> LENGTH: 20
<212> TYPE: DNA
<213> ORGANISM: artificial
<220> FEATURE:
<223> OTHER INFORMATION: 31004 F Primer

<400> SEQUENCE: 13
ctcaccggtc cttcacaatg 20

<210> SEQ ID NO 14
<211> LENGTH: 19
<212> TYPE: DNA
<213> ORGANISM: artificial
<220> FEATURE:
<223> OTHER INFORMATION: 31004 R Primer

<400> SEQUENCE: 14
caaggcgcac gttagacac 19

<210> SEQ ID NO 15
<211> LENGTH: 21
<212> TYPE: DNA
<213> ORGANISM: artificial
<220> FEATURE:
<223> OTHER INFORMATION: pco642297_3 F Primer

<400> SEQUENCE: 15
cgaccgacga tagatggtgt c 21

<210> SEQ ID NO 16
<211> LENGTH: 24
<212> TYPE: DNA
<213> ORGANISM: artificial
<220> FEATURE:
<223> OTHER INFORMATION: pco642297_3 R Primer

<400> SEQUENCE: 16
atgttgctcc aacagatact ttgc 24

<210> SEQ ID NO 17
<211> LENGTH: 23
<212> TYPE: DNA
<213> ORGANISM: artificial
<220> FEATURE:
<223> OTHER INFORMATION: b109.m6 F Primer

<400> SEQUENCE: 17
gctgagttgg atatggtcta tgg 23

<210> SEQ ID NO 18
<211> LENGTH: 20
<212> TYPE: DNA
<213> ORGANISM: artificial
<220> FEATURE:
<223> OTHER INFORMATION: b109.m6 R Primer

<400> SEQUENCE: 18
ttcaggtgct aggtttgtgg 20

<210> SEQ ID NO 19
<211> LENGTH: 19
<212> TYPE: DNA
<213> ORGANISM: artificial
<220> FEATURE:
<223> OTHER INFORMATION: PHM18979 F Primer

<400> SEQUENCE: 19
ggtcaatcgg actacagtg 19

<210> SEQ ID NO 20
<211> LENGTH: 20
<212> TYPE: DNA
<213> ORGANISM: artificial
<220> FEATURE:
<223> OTHER INFORMATION: PHM18979 R Primer

<400> SEQUENCE: 20
aaagcagggt tagtgcgact 20

<210> SEQ ID NO 21
<211> LENGTH: 20
<212> TYPE: DNA
<213> ORGANISM: artificial
<220> FEATURE:
<223> OTHER INFORMATION: b0507L21 F Primer

<400> SEQUENCE: 21
agcaccacac aggagacacg 20

<210> SEQ ID NO 22
<211> LENGTH: 19
<212> TYPE: DNA
<213> ORGANISM: artificial
<220> FEATURE:
<223> OTHER INFORMATION: b0507L21 R Primer

<400> SEQUENCE: 22
gtgcctggag atgttgacg 19

<210> SEQ ID NO 23
<211> LENGTH: 20
<212> TYPE: DNA
<213> ORGANISM: artificial
<220> FEATURE:
<223> OTHER INFORMATION: 2_2 F Primer

<400> SEQUENCE: 23
gagacatggt gtttgcatgg 20

<210> SEQ ID NO 24

<211> LENGTH: 20
<212> TYPE: DNA
<213> ORGANISM: artificial
<220> FEATURE:
<223> OTHER INFORMATION: 2_2 R Primer

<400> SEQUENCE: 24
ttcttgggct ctctctaccg 20

<210> SEQ ID NO 25
<211> LENGTH: 19
<212> TYPE: DNA
<213> ORGANISM: artificial
<220> FEATURE:
<223> OTHER INFORMATION: 156k16 F Primer

<400> SEQUENCE: 25
agtgcacttg gcaacaagc 19

<210> SEQ ID NO 26
<211> LENGTH: 20
<212> TYPE: DNA
<213> ORGANISM: artificial
<220> FEATURE:
<223> OTHER INFORMATION: 156k16 R Primer

<400> SEQUENCE: 26
catgtccagg acctttaccg 20

<210> SEQ ID NO 27
<211> LENGTH: 22
<212> TYPE: DNA
<213> ORGANISM: artificial
<220> FEATURE:
<223> OTHER INFORMATION: b0318i13 F Primer

<400> SEQUENCE: 27
gatcaagatg ggaattcttt cg 22

<210> SEQ ID NO 28
<211> LENGTH: 20
<212> TYPE: DNA
<213> ORGANISM: artificial
<220> FEATURE:
<223> OTHER INFORMATION: b0318i13 R Primer

<400> SEQUENCE: 28
ttccacatcc aacatcaagc 20

<210> SEQ ID NO 29
<211> LENGTH: 19
<212> TYPE: DNA
<213> ORGANISM: artificial
<220> FEATURE:
<223> OTHER INFORMATION: PHM4757 F Primer

<400> SEQUENCE: 29
tcctgaacgc gagcctcta 19

<210> SEQ ID NO 30
<211> LENGTH: 21
<212> TYPE: DNA
<213> ORGANISM: artificial
<220> FEATURE:
<223> OTHER INFORMATION: PHM4757 R Primer

<400> SEQUENCE: 30

```
taacgagtct cgtctccaga a                                               21


<210> SEQ ID NO 31
<211> LENGTH: 23
<212> TYPE: DNA
<213> ORGANISM: artificial
<220> FEATURE:
<223> OTHER INFORMATION: NLB5A F Primer

<400> SEQUENCE: 31

gctgaactag tagcacggca tgt                                             23


<210> SEQ ID NO 32
<211> LENGTH: 22
<212> TYPE: DNA
<213> ORGANISM: artificial
<220> FEATURE:
<223> OTHER INFORMATION: NLB5A R Primer

<400> SEQUENCE: 32

agcggagaga cggatagaga ga                                              22


<210> SEQ ID NO 33
<211> LENGTH: 255
<212> TYPE: DNA
<213> ORGANISM: artificial
<220> FEATURE:
<223> OTHER INFORMATION: NLB5A probe
<220> FEATURE:
<221> NAME/KEY: misc_feature
<222> LOCATION: (78)..(94)
<223> OTHER INFORMATION: n is a, c, g, or t

<400> SEQUENCE: 33

gctgaactag tagcacggca tgtactgtcg ccgccagtcc aggtccaggc gtccagcgag     60

gcagcagcaa acgcagcnnn nnnnnnnnnn nnnncccgcc tcagccgatc cgagacattc    120

ctgtctgggt gagggtgagg ccaaccaacc gcttcgctcc tctcggtaaa tcggcgatcc    180

atccagcgga gccgcaacca aaaagcagag caacgcccaa attaaaaaca gggcagggga    240

aaaaaaaagc tcgca                                                     255


<210> SEQ ID NO 34
<211> LENGTH: 22
<212> TYPE: DNA
<213> ORGANISM: artificial
<220> FEATURE:
<223> OTHER INFORMATION: NLB3A F Primer

<400> SEQUENCE: 34

ggtgtccgca cactcttctt ct                                              22


<210> SEQ ID NO 35
<211> LENGTH: 22
<212> TYPE: DNA
<213> ORGANISM: artificial
<220> FEATURE:
<223> OTHER INFORMATION: NLB3A R Primer

<400> SEQUENCE: 35

aaagcaaatt gaacgcacga gt                                              22


<210> SEQ ID NO 36
<211> LENGTH: 255
<212> TYPE: DNA
```

```
<213> ORGANISM: artificial
<220> FEATURE:
<223> OTHER INFORMATION: NLB3A probe
<220> FEATURE:
<221> NAME/KEY: misc_feature
<222> LOCATION: (122)..(139)
<223> OTHER INFORMATION: n is a, c, g, or t
<220> FEATURE:
<221> NAME/KEY: misc_feature
<222> LOCATION: (248)..(255)
<223> OTHER INFORMATION: n is a, c, g, or t

<400> SEQUENCE: 36

ggtgtccgca cactcttctt ctattgtttg tctactcact ccactcccgt cctcgctcct     60

tccacgaaac tacgttcact agctcgggat gaacagagtc gcctctctct ctgctagtca    120

gnnnnnnnnn nnnnnnnnna cacggatcag tttgtaatta ccgtgacttc attgccacag    180

ctacacaatt gcacgagtca aagtcttttg gctggctcct agcacccaca caaaacaacc    240

tcgcccgnnn nnnnn                                                     255


<210> SEQ ID NO 37
<211> LENGTH: 22
<212> TYPE: DNA
<213> ORGANISM: artificial
<220> FEATURE:
<223> OTHER INFORMATION: PHM2817-26 F Primer

<400> SEQUENCE: 37

atatttacag tttcggagtg gt                                              22


<210> SEQ ID NO 38
<211> LENGTH: 22
<212> TYPE: DNA
<213> ORGANISM: artificial
<220> FEATURE:
<223> OTHER INFORMATION: PHM2817-26 R Primer

<400> SEQUENCE: 38

atctgtgctg ataaaaaaaa gc                                              22


<210> SEQ ID NO 39
<211> LENGTH: 20
<212> TYPE: DNA
<213> ORGANISM: artificial
<220> FEATURE:
<223> OTHER INFORMATION: PHM7446-6 F Primer

<400> SEQUENCE: 39

tggcttacag ctgctctgct                                                 20


<210> SEQ ID NO 40
<211> LENGTH: 22
<212> TYPE: DNA
<213> ORGANISM: artificial
<220> FEATURE:
<223> OTHER INFORMATION: PHM7446-6 R Primer

<400> SEQUENCE: 40

cttggacaaa ttctgatgat tg                                              22


<210> SEQ ID NO 41
<211> LENGTH: 20
<212> TYPE: DNA
<213> ORGANISM: artificial
<220> FEATURE:
<223> OTHER INFORMATION: PHM4582 F Primer
```

<400> SEQUENCE: 41
agtagcctga gtacaatgcc 20

<210> SEQ ID NO 42
<211> LENGTH: 20
<212> TYPE: DNA
<213> ORGANISM: artificial
<220> FEATURE:
<223> OTHER INFORMATION: PHM4582 R Primer

<400> SEQUENCE: 42
atctctgcac accatggcaa 20

<210> SEQ ID NO 43
<211> LENGTH: 23
<212> TYPE: DNA
<213> ORGANISM: artificial
<220> FEATURE:
<223> OTHER INFORMATION: 9g13-3 F primer

<400> SEQUENCE: 43
tcaatctccc aataagctac tcg 23

<210> SEQ ID NO 44
<211> LENGTH: 21
<212> TYPE: DNA
<213> ORGANISM: artificial
<220> FEATURE:
<223> OTHER INFORMATION: 9g13-3 R Primer

<400> SEQUENCE: 44
caagaatgaa gcaggtgaag g 21

<210> SEQ ID NO 45
<211> LENGTH: 18
<212> TYPE: DNA
<213> ORGANISM: artificial
<220> FEATURE:
<223> OTHER INFORMATION: K F Primer

<400> SEQUENCE: 45
tgtagacggt gccgaagc 18

<210> SEQ ID NO 46
<211> LENGTH: 21
<212> TYPE: DNA
<213> ORGANISM: artificial
<220> FEATURE:
<223> OTHER INFORMATION: K R Primer

<400> SEQUENCE: 46
ctgcaaacac gattagtcag g 21

<210> SEQ ID NO 47
<211> LENGTH: 20
<212> TYPE: DNA
<213> ORGANISM: artificial
<220> FEATURE:
<223> OTHER INFORMATION: 6_7 F Primer

<400> SEQUENCE: 47
gggctagctg aagctactgg 20

<210> SEQ ID NO 48

<211> LENGTH: 20
<212> TYPE: DNA
<213> ORGANISM: artificial
<220> FEATURE:
<223> OTHER INFORMATION: 6_7 R Primer

<400> SEQUENCE: 48
tcaccttctt cttcggatgc 20

<210> SEQ ID NO 49
<211> LENGTH: 20
<212> TYPE: DNA
<213> ORGANISM: artificial
<220> FEATURE:
<223> OTHER INFORMATION: 6_8 F Primer

<400> SEQUENCE: 49
ctccgagcac atctctgtcc 20

<210> SEQ ID NO 50
<211> LENGTH: 20
<212> TYPE: DNA
<213> ORGANISM: artificial
<220> FEATURE:
<223> OTHER INFORMATION: 6_8 R Primer

<400> SEQUENCE: 50
aaaccgggtc aaagtctacg 20

<210> SEQ ID NO 51
<211> LENGTH: 20
<212> TYPE: DNA
<213> ORGANISM: artificial
<220> FEATURE:
<223> OTHER INFORMATION: N F Primer

<400> SEQUENCE: 51
acgagctctg tggtttcacc 20

<210> SEQ ID NO 52
<211> LENGTH: 20
<212> TYPE: DNA
<213> ORGANISM: artificial
<220> FEATURE:
<223> OTHER INFORMATION: N R Primer

<400> SEQUENCE: 52
tcgaaaggta tgccttcacc 20

<210> SEQ ID NO 53
<211> LENGTH: 20
<212> TYPE: DNA
<213> ORGANISM: artificial
<220> FEATURE:
<223> OTHER INFORMATION: R F Primer

<400> SEQUENCE: 53
aaccagaaga aatggcatgg 20

<210> SEQ ID NO 54
<211> LENGTH: 21
<212> TYPE: DNA
<213> ORGANISM: artificial
<220> FEATURE:
<223> OTHER INFORMATION: R R Primer

<400> SEQUENCE: 54

```
tctgtgctat ttgtcggaag g                                              21


<210> SEQ ID NO 55
<211> LENGTH: 20
<212> TYPE: DNA
<213> ORGANISM: artificial
<220> FEATURE:
<223> OTHER INFORMATION: S F Primer

<400> SEQUENCE: 55

ggttgcttga tgtgcttacg                                                20


<210> SEQ ID NO 56
<211> LENGTH: 18
<212> TYPE: DNA
<213> ORGANISM: artificial
<220> FEATURE:
<223> OTHER INFORMATION: S R Primer

<400> SEQUENCE: 56

gcattgcctc ttgagtcc                                                  18


<210> SEQ ID NO 57
<211> LENGTH: 20
<212> TYPE: DNA
<213> ORGANISM: artificial
<220> FEATURE:
<223> OTHER INFORMATION: U F Primer

<400> SEQUENCE: 57

ccgtcctgag caacattacc                                                20


<210> SEQ ID NO 58
<211> LENGTH: 20
<212> TYPE: DNA
<213> ORGANISM: artificial
<220> FEATURE:
<223> OTHER INFORMATION: U R Primer

<400> SEQUENCE: 58

ggagatcaac gaacgagacg                                                20


<210> SEQ ID NO 59
<211> LENGTH: 18
<212> TYPE: DNA
<213> ORGANISM: artificial
<220> FEATURE:
<223> OTHER INFORMATION: PHM13395-16 F Primer

<400> SEQUENCE: 59

tccggcgggt ccgcggtg                                                  18


<210> SEQ ID NO 60
<211> LENGTH: 22
<212> TYPE: DNA
<213> ORGANISM: artificial
<220> FEATURE:
<223> OTHER INFORMATION: PHM13395-16 R Primer

<400> SEQUENCE: 60

agacacggtt acttctaacg aa                                             22


<210> SEQ ID NO 61
<211> LENGTH: 22
<212> TYPE: DNA
```

<213> ORGANISM: artificial
<220> FEATURE:
<223> OTHER INFORMATION: PHM34318-12 F Primer

<400> SEQUENCE: 61
gatggaagat gctacatatc ta 22

<210> SEQ ID NO 62
<211> LENGTH: 22
<212> TYPE: DNA
<213> ORGANISM: artificial
<220> FEATURE:
<223> OTHER INFORMATION: PHM3418-12 R Primer

<400> SEQUENCE: 62
agcaaaacaa aatccattat ta 22

<210> SEQ ID NO 63
<211> LENGTH: 18
<212> TYPE: DNA
<213> ORGANISM: artificial
<220> FEATURE:
<223> OTHER INFORMATION: PHM13395-27 F Primer

<400> SEQUENCE: 63
tccggcgggt ccgcggtg 18

<210> SEQ ID NO 64
<211> LENGTH: 22
<212> TYPE: DNA
<213> ORGANISM: artificial
<220> FEATURE:
<223> OTHER INFORMATION: PHM13395-27 R Primer

<400> SEQUENCE: 64
agacacggtt acttctaacg aa 22

<210> SEQ ID NO 65
<211> LENGTH: 21
<212> TYPE: DNA
<213> ORGANISM: artificial
<220> FEATURE:
<223> OTHER INFORMATION: PHM4677-11 F Primer

<400> SEQUENCE: 65
agaagaacta gagcaacagc a 21

<210> SEQ ID NO 66
<211> LENGTH: 22
<212> TYPE: DNA
<213> ORGANISM: artificial
<220> FEATURE:
<223> OTHER INFORMATION: PHM4677-11 R Primer

<400> SEQUENCE: 66
aatctcaact caacctccat aa 22

<210> SEQ ID NO 67
<211> LENGTH: 20
<212> TYPE: DNA
<213> ORGANISM: artificial
<220> FEATURE:
<223> OTHER INFORMATION: PHM15992-3 F Primer

<400> SEQUENCE: 67
tataccggca acattgggag 20

<210> SEQ ID NO 68
<211> LENGTH: 22
<212> TYPE: DNA
<213> ORGANISM: artificial
<220> FEATURE:
<223> OTHER INFORMATION: PHM15992-3 R Primer

<400> SEQUENCE: 68
gcatttcttt acactgcaac aa 22

<210> SEQ ID NO 69
<211> LENGTH: 23
<212> TYPE: DNA
<213> ORGANISM: artificial
<220> FEATURE:
<223> OTHER INFORMATION: NLB17_A F Primer

<400> SEQUENCE: 69
gtttgttctt cgatttgaag gga 23

<210> SEQ ID NO 70
<211> LENGTH: 23
<212> TYPE: DNA
<213> ORGANISM: artificial
<220> FEATURE:
<223> OTHER INFORMATION: NLB17_A R Primer

<400> SEQUENCE: 70
accgttttcg aggtaaaatg aag 23

<210> SEQ ID NO 71
<211> LENGTH: 21
<212> TYPE: DNA
<213> ORGANISM: artificial
<220> FEATURE:
<223> OTHER INFORMATION: NLB17_E F Primer

<400> SEQUENCE: 71
ttcctcacga gctctgtggt t 21

<210> SEQ ID NO 72
<211> LENGTH: 20
<212> TYPE: DNA
<213> ORGANISM: artificial
<220> FEATURE:
<223> OTHER INFORMATION: NLB17_E R Primer

<400> SEQUENCE: 72
catgctgact agtggtgcgc 20

<210> SEQ ID NO 73
<211> LENGTH: 26
<212> TYPE: DNA
<213> ORGANISM: artificial
<220> FEATURE:
<223> OTHER INFORMATION: NLB17_3 F Primer

<400> SEQUENCE: 73
caagtaggct tcttgtatcc aaattc 26

<210> SEQ ID NO 74
<211> LENGTH: 22
<212> TYPE: DNA
<213> ORGANISM: artificial
<220> FEATURE:

<223> OTHER INFORMATION: NLB17_3 R Primer

<400> SEQUENCE: 74
gccgagtcga aacaagttga gt 22

<210> SEQ ID NO 75
<211> LENGTH: 21
<212> TYPE: DNA
<213> ORGANISM: artificial
<220> FEATURE:
<223> OTHER INFORMATION: NLB18_A F Primer

<400> SEQUENCE: 75
ttgttcttcg atttgaaggg c 21

<210> SEQ ID NO 76
<211> LENGTH: 23
<212> TYPE: DNA
<213> ORGANISM: artificial
<220> FEATURE:
<223> OTHER INFORMATION: NLB18_A R Primer

<400> SEQUENCE: 76
accgttttcg aggtaaaatg aac 23

<210> SEQ ID NO 77
<211> LENGTH: 21
<212> TYPE: DNA
<213> ORGANISM: artificial
<220> FEATURE:
<223> OTHER INFORMATION: NLB18_E F Primer

<400> SEQUENCE: 77
ttcctcacga gctctgtggt c 21

<210> SEQ ID NO 78
<211> LENGTH: 25
<212> TYPE: DNA
<213> ORGANISM: artificial
<220> FEATURE:
<223> OTHER INFORMATION: NLB18_E R Primer

<400> SEQUENCE: 78
gtttacatgc tgactagtgg tgcat 25

<210> SEQ ID NO 79
<211> LENGTH: 19
<212> TYPE: DNA
<213> ORGANISM: artificial
<220> FEATURE:
<223> OTHER INFORMATION: Sequencing tail added to F primers

<400> SEQUENCE: 79
ggaaacagct atgaccatg 19

<210> SEQ ID NO 80
<211> LENGTH: 18
<212> TYPE: DNA
<213> ORGANISM: artificial
<220> FEATURE:
<223> OTHER INFORMATION: Sequencing tail added to R primers

<400> SEQUENCE: 80
tgtaaaacga cggccagt 18

```
<210> SEQ ID NO 81
<211> LENGTH: 478
<212> TYPE: DNA
<213> ORGANISM: artificial
<220> FEATURE:
<223> OTHER INFORMATION: PHM13395 reference sequence

<400> SEQUENCE: 81

aagtatcggg aaagtcccag tcacaaaatc cggcgggtcc gcggtggcgc ccggacgcaa     60

ggaaaagacg gagatcgggg aggtctccac cgagacgtcc gcggcggtgc gcaagaggag    120

aaaggccgac ggcagcagct cccctggcac tccggtttct acgacggata tgcactgccc    180

tcagtgcggc acccatctca tgctaacact gaacatggcg gagtccaaat cggagacggg    240

gctcgcgaag gacgagtcgg ccaccgccgc gcctgatcaa ggcgggacgg gtgagtcttc    300

acagaagaat gttcgggttc ggttccatca gttcctgtga gatccagggt tccttcctgc    360

ccagacaaat cctgggaaac agagccatgg tttctcgtct gttatttgga agaacgaaat    420

aagaagattt tagattaaga attcgttaga ataaccttaa ttttaattaa atagtgaa      478


<210> SEQ ID NO 82
<211> LENGTH: 589
<212> TYPE: DNA
<213> ORGANISM: artificial
<220> FEATURE:
<223> OTHER INFORMATION: PHM4677 reference sequence

<400> SEQUENCE: 82

cccagtcaca acgagaagaa ctagagcaac agcagattcc tcagtcgaag caatctggag     60

tgctgataca gtcacgcagg acacgggagg tgacatcaga cacaaagaga gatggtcgtt    120

tccaaaccgg agctcagtat ggtgatgaaa ctgagagtgt gacaagtaag acacaagtcc    180

atcaaggatt caacagctca agtactgaac ggagtgaaag gagggatcca agtgtgtacc    240

ccagggttgc agtacagcgc tcttcgtcta aagctgagca gattgaatct ccgatggaga    300

gagggaagcc acaaggagct gaaatgagaa gcaccttatt tcgaggaaat gaagaggaca    360

cagaaacctc atctggaact ccaaaagaaa gcacccccaa aacacccccct gcacatgttc   420

atcccaagct tccaacagac tatgattctt tcgccgcaca ttttaggtct cttcgaacaa    480

accggcctta ggtttacacg acatatagag tttggagttt cagttgaatt aagtcatata    540

tacgatacta tgatacgttt tatggagtga ttattactaa cgttattaa                589


<210> SEQ ID NO 83
<211> LENGTH: 651
<212> TYPE: DNA
<213> ORGANISM: artificial
<220> FEATURE:
<223> OTHER INFORMATION: PHM3418 reference sequence

<400> SEQUENCE: 83

gasggatgga agatgctaca tatctacagg gggttttctc acacaagact cactcttgaa     60

tattaaatgt ccagtcagta ttgttcttca gaatctgaaa tcttaataag tacagatata    120

cacggagaat tgggtgaatt cacccgggca acaagaagac aactcgtggc aggcttttgt    180

gtacatacct cctcaagaca gatgggaagt cttgaaggta aattatcgtt ttctatcgat    240

caacatccag agtatgtgac ttttttttagt gatgaagaaa ccgttcccat tccatacaga   300

tccctcttga tcgctattta cccacatgga gaggaaatgt gatccaggca aagttggaaa    360

tgaaccctgc tcggatcgtg gggatgtctc tctctgtaaa cgcagaaggc ggtgttcctg    420
```

```
gcgccaagac tgggcctggt gattttaggc ttgatgttgc ttggatcaaa gcgttgagag    480

ctttgtgaac tccacaagtc atagttttat ttcacatcgg ccctttcctt ctttatcacc    540

ctgctccagt ggcgccgctg aactcatcag ccgaccacaa ccacaggagt aaccatagca    600

cagattgcca actcctttat gcacttaata atgatttttt aatatctwtt t             651


<210> SEQ ID NO 84
<211> LENGTH: 703
<212> TYPE: DNA
<213> ORGANISM: artificial
<220> FEATURE:
<223> OTHER INFORMATION: PHM15992 reference sequence

<400> SEQUENCE: 84

atttttgga agctgaacaa tttccatgaa gaaggtactc ttgtttttta gatattggag      60

cgaggcattt accatccaaa gatggggttc ttgctttctt aaagaaaaaa aagtagctgt    120

aagctgattt accaggttga ccctagttag atatcttaaa tttgaaatat atgctgtggc    180

tttattgtga ggtaataata tttttctcag ccatgttagt tacatccaag aattgggctg    240

tttactaagt ttcttgtttt tttgttgtac cagaagtgaa atcctagatt aatacatgga    300

ggtcatgaaa caattaatag aaaatgctac ttttttgtac taacatttgt ttctcttgtg    360

agcaggcctt gtatgagaca ttgattcggc aggatgagct gcttgcatat attgaccaac    420

aacagacagc caaattttgt gtaagttaca gccgttcgta tagtttgcct tttcctttca    480

agaacatatc atcttaatgc ttccctcttc tagtcaaggg taccaaatac gcaatttctt    540

atttgtccat tcatcatttg cagcggcaga agttctgttt ctaagtactg gagtacctgc    600

cacctatttt cgtctctttg gagatcgcat gcagctattg tggacccagt atacttgcaa    660

atgttttcat atttgttgca gttatggata attgggaaaa acc                      703


<210> SEQ ID NO 85
<211> LENGTH: 466
<212> TYPE: DNA
<213> ORGANISM: artificial
<220> FEATURE:
<223> OTHER INFORMATION: PHM2817 reference sequence

<400> SEQUENCE: 85

aagggttagg agaagatccc agtcaaaacg atatttacag tttcggagtg gtgctgttag      60

aatgtgcgac cgctagggat ccagtcgatt actctaagcc tgcagatgag gtacgagttc    120

tccctgtttc agacaattgg tgtgattgta tttccattta cttcttaaac ctcttctatt    180

gtttgtttca ggtgaatctc atagagtggc ttaaaatgat ggtccactca ccagtaagag    240

ggcagaggag gtagtggatc caaacctcaa tgttaagcca ccaaaacgtg ccctcaagcg    300

gacaatcctg gttggcttca agtgtgtcga tcctgacgct gacaagaggc caaagatgag    360

tcacgttgtc cagatgcttg aagcagttca gaatgcatat catgaagtac tcatctcatc    420

ctaacatttt ctttctcgtg ctctgctttt tatcgcacaa aaaaaa                   466


<210> SEQ ID NO 86
<211> LENGTH: 486
<212> TYPE: DNA
<213> ORGANISM: artificial
<220> FEATURE:
<223> OTHER INFORMATION: PHM7446 reference sequence

<400> SEQUENCE: 86

aaaaaaaacc aaatacaaaa tggctaaaga tgcgggaagt cccagtcaaa acgtggctta      60
```

cagctgctct gcttcagctt gctcctgata aacagtactt gctgcctagt tcatcaacta 120
gtacaagttt gaaccatggt ttgctggttg gttcctttcc tgataggggt atagggaggt 180
cgtcagcagt tgagcataaa tgtaacctgg caggcacgtc ttatggggaa ggaactgttg 240
aacacacaga aaatggtcat gtgttatcaa ccagttctgt caaaggaaat gagggaacta 300
aaaacagaaa agcggacaat gaaatgatct ggcaagctgt gcttgagagt atccaatcag 360
atacattgag aaaaatgatg gctaaagagg ccaggctaaa ctctgtcagc ctaggaacag 420
gtaagattct caatctgtca tccatatcag ttttacaatc atcagaattt ccaactttgc 480
tgtaaa 486

<210> SEQ ID NO 87
<211> LENGTH: 707
<212> TYPE: DNA
<213> ORGANISM: artificial
<220> FEATURE:
<223> OTHER INFORMATION: NLB17_A reference sequence

<400> SEQUENCE: 87
gcatatgggc ctgcctgttc gcataagtac accctccgtc taaaaagaat aaaaatctca 60
tttcttgatg agtcaaaaag ttcaaattta agaaaatata tgttatgaca cgaatattta 120
taatgcgtaa taagtactgc taaattaatt ttaaaataaa attttcataa taaacctatt 180
tgaagataca agtattggta ctatttctaa taaatctaat caaactggtg ttatatcttt 240
tgtaacaaat ttgtgcttta tgtttctggt gacgtgaatc agcttaatct tgctcaaatc 300
taacattgtc ttttgttcgt tggcatacag gatcaaaaag aaaagaagca gcacctattg 360
ttggtaagag cctatagtca atacacatgt tcatttcgtc taaaagagca gaagaaaagc 420
atgtgatgaa ttattgccat gtcatgttta aaatacagaa ttctcaaaaa caaaaaaaaa 480
cttggaatcc actaaccact gatagcattg tagaaaattt catcctcccg ttgggcagta 540
cactgatgag tttacatgct gactagtggt gcgcatttgt tctttgccaa ttgagttttt 600
agaatgcttt gcagctgaat tcacatgtga tttttttttgt gatgcaggtg ctgttgccgt 660
tgcattcctg tgtctagtca ttctcacatc cttcttggct gtagata 707

<210> SEQ ID NO 88
<211> LENGTH: 961
<212> TYPE: DNA
<213> ORGANISM: artificial
<220> FEATURE:
<223> OTHER INFORMATION: NLB17_E reference sequence

<400> SEQUENCE: 88
gttctttgcc attgagtttt tagaatgctt tgcagctgaa ttcacatgtg attttttttt 60
gtgatgcagg tgctgttgcc gttgccgttg cattcctgtg tctagtcatt ctcacatcct 120
tcttggcttg tagatatggt ttgcttccct tcaaatcgaa gaacaaacca gggacaagga 180
ttgagtcctt cctacagaag aacgagagca tacatccgaa aagatacacc tacgcggacg 240
tgaaaagaat gacaaaatcc ttcgctgtga agctaggcca aggtgggttt ggtgctgtat 300
acaaaggcag cctccacgat ggccgacagg tagcagtcaa gatgctcaag gacacccaag 360
gtgacggcga ggaattcatg aacgaggtgg ctagcatcag caggacttct catgtcaacg 420
tcgtgacact tctagggttt tgcttgcaag ggtcgaaaag agcactgatc tacgagtaca 480
tgcccaatgg ttcgctcgaa aggtatgcct tcaccggtga catgaacagt gagaatttgc 540

```
taacctggga aagactattt gacatagcaa ttggcacggc cagagggctc gaatacctac    600

accggggatg caacactcgg atcgtgcatt ttgacatcaa gccacacaac atcctgttag    660

accaggattt ctgccctaag atctctgact ttggactggc caagctatgt ctgaacaaag    720

agagcgctat ctccattgtt ggcgcaagag ggacgatagg gtatatcgcc ccggaggtct    780

actcaaagca atttggaaca ataagcagca agtctgatgt ctatagctat gggatgatgg    840

tccttgagat ggttggagca agggacagga atacaagcgc agatagtgac catagcagcc    900

aatatttccc tcagtggctt tatgagcatt tggacgacta ttgtgttggt gctccgagat    960

t                                                                    961
```

```
<210> SEQ ID NO 89
<211> LENGTH: 539
<212> TYPE: DNA
<213> ORGANISM: artificial
<220> FEATURE:
<223> OTHER INFORMATION: NLB17_3 reference sequence

<400> SEQUENCE: 89

cagctatgac catggccgag tcgaaacaag ttgagttcat gacgagtcga gcaagctcac     60

aatccacgag taattttttt ccagtcctac ctaagactaa agtttagtcc tagaactaaa    120

ttttagtctc tatctgtttg gttctataaa ctaaacaggt tcagaacaaa taaaatacac    180

tatagaaaaa ctgaaatacc cttctatgat taaggcgtca ctaagcgaga gcaataaatg    240

aagggtagag agagaaataa atatgtttta gtctctttta gctaccattt gagagagtaa    300

agactaaaat gaaaggtccc ttgtaggctt tggtgttttg gatgacaaca caattaaagg    360

tctaattaag atgttaagtg ttgagcaggt acttagtgaa aagcttccaa ggctcaacac    420

atggagacaa gagtgatata ccatatataa gctgagttgg atatggtcta tggatatcag    480

gagtcaaagt gaaagattgt cattgatcaa gaatttggat acaagaagcc tacttgact     539
```

```
<210> SEQ ID NO 90
<211> LENGTH: 784
<212> TYPE: DNA
<213> ORGANISM: artificial
<220> FEATURE:
<223> OTHER INFORMATION: NL B18_A reference sequence

<400> SEQUENCE: 90

aaagcatatg ggcctgcctg ttcgcataag tacaccctcc gtctaaaaaa gaataaaaat     60

ctcatttctt gatgagtcaa aaaagttcaa atttaagaaa atatatgtta cgacacgaat    120

atttataatg cgtaataagt actgctagat taattctaaa ataaaatttt cataataaac    180

ctatttgaag atacaagtat attggtacta tttctaataa atctaatcaa actggtgtta    240

tatcttttgg aacaaatttg tgctttatgt ttctggttga cgtgaatcag cttaatcttg    300

ctcaaatcta acattgtctt ttgttcgttg gcatacagga tcaacaaaaa ggaaagaagc    360

agcatctatt gttggtaaga gcctatagtc aataataccc atgttcattt cgtctaaaag    420

agcagaagaa aagcatatga tgaattattg ccatgtcttg tttaaaatac agaattctca    480

aaaacaaaaa caaaaaaaaa cttggaatcc actaaccagt aaccactgat agcattgtag    540

aaaatttcat cctccctttg ggcaatacac actgatgagt ttacatgctg actagtggtg    600

cgcatttgtt cttttgccaa ttgaattttt agaatgcttt gcagctgaat tcacttgtgg    660

tgtttttttt ttgtgtgatg caggtgctgt tgttgccgtt gcattcctgt gtctagtcat    720

tctcacatgc ttcttggctt gtagacatgg ttcgctgccc ttcaaatcga agaacaaact    780
```

```
ggcc                                                                784

<210> SEQ ID NO 91
<211> LENGTH: 624
<212> TYPE: DNA
<213> ORGANISM: artificial
<220> FEATURE:
<223> OTHER INFORMATION: NLB18_E reference sequence

<400> SEQUENCE: 91

ttaatctcgg agcaccaaca caatagtcgt ccaaatgctc ataaagccac tgagggaaat     60
attggctgct atggtcacta ctatctgcgc ttgcgcttgt attcctttcc cttgctccaa    120
ccatctcaag gaccatcatc ccatagctat agacatcaga cttgctgctg attgttccaa    180
attgctttga gtagacctcc ggggcgatat accctatcgt ccctcttgcg ccaacaatgg    240
agatagcgct ctctttgttc agacatagct tggccagtcc aaagtcagag atcttagggc    300
agaaatcctg gtctaacagg atgttgtgtg gcttgatgtc aaaatgcacg atccgagtgt    360
tgcatccccg gtgtaggtat tcgagccctc tggccgtgtg ccaattgcta tgtcaaatag    420
tctttcccag gttagcaaat tctcactgtt catgtcaccg gtgaaggcat acctttcgag    480
cgaaccattg ggcatgtact cgtagatcag tgctcttttc gacccttgca agcaaaaccc    540
tagaagtgtc acgacgttga catgagaagt cctgctgatg ctagccacct cgttcatgaa    600
ttcctcgccg tcaccttggg tgtc                                           624

<210> SEQ ID NO 92
<211> LENGTH: 1463
<212> TYPE: DNA
<213> ORGANISM: Zea mays

<400> SEQUENCE: 92

gttggaggct tggagctaac aacgcggctt gatgagggtg aacccagccc cacctcgtct     60
accacgtctt ctcctcggca tggctgctca cctaccacgt ctccccgtcc tcctcctcgt    120
cctcctcgct gcccatgtcg tctccacctc cacccgtgcc gagcctcctc ttccgagcac    180
ttacaacgtc tccatgttct cggaatcgtt ctggtgcggc ggaatcgagt tggaatggaa    240
tcggacatgg gaggatcagt gtggccagtg cgagggattg ggctccggcg gacggtgcgc    300
ctacagccag aagagagaat tcctgggctg cttgtgcagc ggagggaagg tgggcaaccc    360
gttctgcaaa ccatcgacat cgagatcaaa aagaaaagaa gcagcaccta ttgttggtgc    420
tgttgccgtt gcattcctgt gtctagtcat tctcacatcc ttcttggctt gtagatatgg    480
tttgcttccc ttcaaatcga agaacaaacc agggacaagg attgagtcct tcctacagaa    540
gaacgagagc atacatccga aaagatacac ctacgcggac gtgaaaagaa tgacaaaatc    600
cttcgctgtg aagctaggcc aaggtgggtt tggtgctgta tacaaaggca gcctccacga    660
tggccgacag gtagcagtca agatgctcaa ggacacccaa ggtgacggcg aggaattcat    720
gaacgaggtg gctagcatca gcaggacttc tcatgtcaac gtcgtgacac ttctagggtt    780
ttgcttgcaa gggtcgaaaa gagcactgat ctacgagtac atgcccaatg gttcgctcga    840
aaggtatgcc ttcaccggtg acatgaacag tgagaatttg ctaacctggg aaagactatt    900
tgacatagca attggcacgg ccagagggct cgaataccta caccggggat gcaacactcg    960
gatcgtgcat tttgacatca agccacacaa catcctgtta gaccaggatt tctgccctaa   1020
gatctctgac tttggactgg ccaagctatg tctgaacaaa gagagcgcta tctccattgt   1080
```

```
tggcgcaaga gggacgatag ggtatatcgc cccggaggtc tactcaaagc aatttggaac   1140

aataagcagc aagtctgatg tctatagcta tgggatgatg gtccttgaga tggttggagc   1200

aagggacagg aatacaagcg cagatagtga ccatagcagc caatatttcc ctcagtggct   1260

ttatgagcat ttggacgact attgtgttgg tgcttccgag attaatggtg aaaccacaga   1320

gctcgtgagg aagatgatag ttgtaggtct gtggtgcata caagtgattc cgactgatcg   1380

accaacaatg acgagagtcg tcgagatgtt ggaagggagc acaagtaatc tagagttgcc   1440

acccagagtt cttttgagct gac                                           1463
```

<210> SEQ ID NO 93
<211> LENGTH: 476
<212> TYPE: PRT
<213> ORGANISM: Zea mays

<400> SEQUENCE: 93

```
Met Arg Val Asn Pro Ala Pro Pro Arg Leu Pro Arg Leu Leu Leu Gly
1               5                   10                  15

Met Ala Ala His Leu Pro Arg Leu Pro Val Leu Leu Leu Val Leu Leu
            20                  25                  30

Ala Ala His Val Val Ser Thr Ser Thr Arg Ala Glu Pro Pro Leu Pro
        35                  40                  45

Ser Thr Tyr Asn Val Ser Met Phe Ser Glu Ser Phe Trp Cys Gly Gly
    50                  55                  60

Ile Glu Leu Glu Trp Asn Arg Thr Trp Glu Asp Gln Cys Gly Gln Cys
65                  70                  75                  80

Glu Gly Leu Gly Ser Gly Gly Arg Cys Ala Tyr Ser Gln Lys Arg Glu
                85                  90                  95

Phe Leu Gly Cys Leu Cys Ser Gly Gly Lys Val Gly Asn Pro Phe Cys
            100                 105                 110

Lys Pro Ser Thr Ser Arg Ser Lys Arg Lys Glu Ala Ala Pro Ile Val
        115                 120                 125

Gly Ala Val Ala Val Ala Phe Leu Cys Leu Val Ile Leu Thr Ser Phe
    130                 135                 140

Leu Ala Cys Arg Tyr Gly Leu Leu Pro Phe Lys Ser Lys Asn Lys Pro
145                 150                 155                 160

Gly Thr Arg Ile Glu Ser Phe Leu Gln Lys Asn Glu Ser Ile His Pro
                165                 170                 175

Lys Arg Tyr Thr Tyr Ala Asp Val Lys Arg Met Thr Lys Ser Phe Ala
            180                 185                 190

Val Lys Leu Gly Gln Gly Gly Phe Gly Ala Val Tyr Lys Gly Ser Leu
        195                 200                 205

His Asp Gly Arg Gln Val Ala Val Lys Met Leu Lys Asp Thr Gln Gly
    210                 215                 220

Asp Gly Glu Glu Phe Met Asn Glu Val Ala Ser Ile Ser Arg Thr Ser
225                 230                 235                 240

His Val Asn Val Val Thr Leu Leu Gly Phe Cys Leu Gln Gly Ser Lys
                245                 250                 255

Arg Ala Leu Ile Tyr Glu Tyr Met Pro Asn Gly Ser Leu Glu Arg Tyr
            260                 265                 270

Ala Phe Thr Gly Asp Met Asn Ser Glu Asn Leu Leu Thr Trp Glu Arg
        275                 280                 285

Leu Phe Asp Ile Ala Ile Gly Thr Ala Arg Gly Leu Glu Tyr Leu His
    290                 295                 300
```

```
Arg Gly Cys Asn Thr Arg Ile Val His Phe Asp Ile Lys Pro His Asn
305                 310                 315                 320

Ile Leu Leu Asp Gln Asp Phe Cys Pro Lys Ile Ser Asp Phe Gly Leu
                325                 330                 335

Ala Lys Leu Cys Leu Asn Lys Glu Ser Ala Ile Ser Ile Val Gly Ala
            340                 345                 350

Arg Gly Thr Ile Gly Tyr Ile Ala Pro Glu Val Tyr Ser Lys Gln Phe
        355                 360                 365

Gly Thr Ile Ser Ser Lys Ser Asp Val Tyr Ser Tyr Gly Met Met Val
    370                 375                 380

Leu Glu Met Val Gly Ala Arg Asp Arg Asn Thr Ser Ala Asp Ser Asp
385                 390                 395                 400

His Ser Ser Gln Tyr Phe Pro Gln Trp Leu Tyr Glu His Leu Asp Asp
                405                 410                 415

Tyr Cys Val Gly Ala Ser Glu Ile Asn Gly Glu Thr Thr Glu Leu Val
            420                 425                 430

Arg Lys Met Ile Val Val Gly Leu Trp Cys Ile Gln Val Ile Pro Thr
        435                 440                 445

Asp Arg Pro Thr Met Thr Arg Val Val Glu Met Leu Glu Gly Ser Thr
    450                 455                 460

Ser Asn Leu Glu Leu Pro Pro Arg Val Leu Leu Ser
465                 470                 475
```

<210> SEQ ID NO 94
<211> LENGTH: 2064
<212> TYPE: DNA
<213> ORGANISM: Zea mays

<400> SEQUENCE: 94

```
tccacctcgt ctaccacgtc ttctccccgc catggctgct caccagcctc acctctccgt     60

cctcctcctc gtcctcctcg ctgcccatgt cgtctccacc tccgcccatg gcgagcctcc    120

tcttccgagc ccttacaaca cctccgccca tggcgagcct cctcttccga gcacttacaa    180

cgcctccatg tgctcgtcgt tctggtgtgg cggcgtcgag atccgctacc cgttctatct    240

tgccaacgca atcgccgact acagcgggag ctactactcc tgcggctaca ccgacttgag    300

cgtttcctgc gaactcgagg tcgaggggtc gccgacgacc tggaccccta ccatccgtct    360

cggcggcggc gactacaccg tcaagaacat ctcctacctc tacgaccagc agaccatctc    420

actggcggac agagatgtgc tcggaggcgg cggctgcccc gtcgtccgcc acaacgtcag    480

cttcgacgag acgtggctgc acctgcacaa cgccagcgcc ttcgacaacc tcaccttctt    540

cttcggatgc cactgggggc cacggaatac accgcctgaa tttgccgact acaacatcag    600

ctgcgccggg ttcaatactc caactatcag cggtggaagg tccttcgtgt tcaagactgg    660

agatcttgac gaacaagagg agcaggagtt ggctttacac tgcgacgagg ttttctccgt    720

gccagtgaga agagatgctc tgcaggcgat cgtcagcaac ttcagcctca cacgggacgg    780

gtacggcgag gtgcttaggc aggggttcga gttggaatgg aatcggacat cggaggatca    840

gtgtggccgg tgcgagggat cgggctccgg cggatggtgc gcctacagcc agaagagaga    900

attcctgggc tgcttgtgca gcggagggaa ggtgggcagc ccgttctgca aaccatcgag    960

atcaaaaagg aaagaaggac ctattgttgg tgctgttgcc gttgcattcc tgtgtctagt   1020

cattctcaca tgcttcttgg cttgtagaca tggttcgctg cccttcaaat cggagaacaa   1080

accagggaca aggattgagt ccttcctaca gaagaacgag agtatacatc cgaaaagata   1140
```

```
cacctacgcg gacgtgaaaa gaatgacaaa atccttcgct gtgaagctag gccaaggtgg   1200

gtttggtgct gtatacaaag gcagcctcca cgatggccga caggtagcag tcaagatgct   1260

gaaggacacc caaggtgacg gcgaggaatt catgaacgag gtggctagca tcagcaggac   1320

ttctcatgtc aacgtcgtga cacttctagg gttttgcttg caagggtcga aaagagcact   1380

gatctacgag tacatgccca atggttcgct cgaaaggtat gccttcaccg gtgacatgaa   1440

cagtgagaat ttgctaacct gggaaaggct atttgacata gcaattggca cggccagagg   1500

gctcgaatac ctacaccggg gatgcaacac tcggatcgtg cattttgaca tcaagccaca   1560

caacatcctg ttagaccagg atttctgtcc taagatctct gactttggac tggccaagct   1620

atgtctgaac aaagagagcg ctatctccat tgctggcgca agagggacga tagggtatat   1680

cgccccggag gtctactcaa agcaatttgg aataataagc agcaagtctg atgtctatag   1740

ctatgggatg atggtccttg agatggttgg agcaagggac aggaatacaa gcgcagatag   1800

tgaccatagc agccaatatt tccctcagtg gctttatgaa catttggacg actattgtgt   1860

tggtgcttcc gagattaatg gtgagaccac agagctcgtg aggaagatga tagttgtagg   1920

tctgtggtgc atacaagtga ttccgactga tcgaccaaca atgacgagag tcgtcgagat   1980

gttggaaggg agcacaagta atctagagtt gccacccaga gttctcttga gctgacaaag   2040

cgtagatatt tttcctatca aatg                                          2064
```

<210> SEQ ID NO 95
<211> LENGTH: 667
<212> TYPE: PRT
<213> ORGANISM: Zea mays

<400> SEQUENCE: 95

```
Met Ala Ala His Gln Pro His Leu Ser Val Leu Leu Leu Val Leu Leu
1               5                   10                  15

Ala Ala His Val Val Ser Thr Ser Ala His Gly Glu Pro Pro Leu Pro
            20                  25                  30

Ser Pro Tyr Asn Thr Ser Ala His Gly Glu Pro Pro Leu Pro Ser Thr
        35                  40                  45

Tyr Asn Ala Ser Met Cys Ser Ser Phe Trp Cys Gly Gly Val Glu Ile
    50                  55                  60

Arg Tyr Pro Phe Tyr Leu Ala Asn Ala Ile Ala Asp Tyr Ser Gly Ser
65                  70                  75                  80

Tyr Tyr Ser Cys Gly Tyr Thr Asp Leu Ser Val Ser Cys Glu Leu Glu
                85                  90                  95

Val Glu Gly Ser Pro Thr Thr Trp Thr Pro Thr Ile Arg Leu Gly Gly
            100                 105                 110

Gly Asp Tyr Thr Val Lys Asn Ile Ser Tyr Leu Tyr Asp Gln Gln Thr
        115                 120                 125

Ile Ser Leu Ala Asp Arg Asp Val Leu Gly Gly Gly Gly Cys Pro Val
    130                 135                 140

Val Arg His Asn Val Ser Phe Asp Glu Thr Trp Leu His Leu His Asn
145                 150                 155                 160

Ala Ser Ala Phe Asp Asn Leu Thr Phe Phe Phe Gly Cys His Trp Gly
                165                 170                 175

Pro Arg Asn Thr Pro Pro Glu Phe Ala Asp Tyr Asn Ile Ser Cys Ala
            180                 185                 190

Gly Phe Asn Thr Pro Thr Ile Ser Gly Gly Arg Ser Phe Val Phe Lys
        195                 200                 205
```

```
Thr Gly Asp Leu Asp Glu Gln Glu Glu Gln Glu Leu Ala Leu His Cys
    210                 215                 220

Asp Glu Val Phe Ser Val Pro Val Arg Arg Asp Ala Leu Gln Ala Ile
225                 230                 235                 240

Val Ser Asn Phe Ser Leu Thr Arg Asp Gly Tyr Gly Glu Val Leu Arg
                245                 250                 255

Gln Gly Phe Glu Leu Glu Trp Asn Arg Thr Ser Glu Asp Gln Cys Gly
            260                 265                 270

Arg Cys Glu Gly Ser Gly Ser Gly Gly Trp Cys Ala Tyr Ser Gln Lys
        275                 280                 285

Arg Glu Phe Leu Gly Cys Leu Cys Ser Gly Gly Lys Val Gly Ser Pro
    290                 295                 300

Phe Cys Lys Pro Ser Arg Ser Lys Arg Lys Glu Gly Pro Ile Val Gly
305                 310                 315                 320

Ala Val Ala Val Ala Phe Leu Cys Leu Val Ile Leu Thr Cys Phe Leu
                325                 330                 335

Ala Cys Arg His Gly Ser Leu Pro Phe Lys Ser Glu Asn Lys Pro Gly
            340                 345                 350

Thr Arg Ile Glu Ser Phe Leu Gln Lys Asn Glu Ser Ile His Pro Lys
        355                 360                 365

Arg Tyr Thr Tyr Ala Asp Val Lys Arg Met Thr Lys Ser Phe Ala Val
    370                 375                 380

Lys Leu Gly Gln Gly Gly Phe Gly Ala Val Tyr Lys Gly Ser Leu His
385                 390                 395                 400

Asp Gly Arg Gln Val Ala Val Lys Met Leu Lys Asp Thr Gln Gly Asp
                405                 410                 415

Gly Glu Glu Phe Met Asn Glu Val Ala Ser Ile Ser Arg Thr Ser His
            420                 425                 430

Val Asn Val Val Thr Leu Leu Gly Phe Cys Leu Gln Gly Ser Lys Arg
        435                 440                 445

Ala Leu Ile Tyr Glu Tyr Met Pro Asn Gly Ser Leu Glu Arg Tyr Ala
    450                 455                 460

Phe Thr Gly Asp Met Asn Ser Glu Asn Leu Leu Thr Trp Glu Arg Leu
465                 470                 475                 480

Phe Asp Ile Ala Ile Gly Thr Ala Arg Gly Leu Glu Tyr Leu His Arg
                485                 490                 495

Gly Cys Asn Thr Arg Ile Val His Phe Asp Ile Lys Pro His Asn Ile
            500                 505                 510

Leu Leu Asp Gln Asp Phe Cys Pro Lys Ile Ser Asp Phe Gly Leu Ala
        515                 520                 525

Lys Leu Cys Leu Asn Lys Glu Ser Ala Ile Ser Ile Ala Gly Ala Arg
    530                 535                 540

Gly Thr Ile Gly Tyr Ile Ala Pro Glu Val Tyr Ser Lys Gln Phe Gly
545                 550                 555                 560

Ile Ile Ser Ser Lys Ser Asp Val Tyr Ser Tyr Gly Met Met Val Leu
                565                 570                 575

Glu Met Val Gly Ala Arg Asp Arg Asn Thr Ser Ala Asp Ser Asp His
            580                 585                 590

Ser Ser Gln Tyr Phe Pro Gln Trp Leu Tyr Glu His Leu Asp Asp Tyr
        595                 600                 605

Cys Val Gly Ala Ser Glu Ile Asn Gly Glu Thr Thr Glu Leu Val Arg
    610                 615                 620

Lys Met Ile Val Val Gly Leu Trp Cys Ile Gln Val Ile Pro Thr Asp
```

```
625                 630                 635                 640

Arg Pro Thr Met Thr Arg Val Val Glu Met Leu Glu Gly Ser Thr Ser
                645                 650                 655

Asn Leu Glu Leu Pro Pro Arg Val Leu Leu Ser
            660                 665


<210> SEQ ID NO 96
<211> LENGTH: 2061
<212> TYPE: DNA
<213> ORGANISM: Zea mays

<400> SEQUENCE: 96

tccacctcgt ctaccacgtc ttctcctcgc catggctgct cacctaccac gcctccccgt     60

cctcctcctc gtcctcctcg ctgctcatgt cgtctccacc tccgcccatg ccgagcctcc    120

tcttccgagc ccttacagca cctccgccca tggcgagcct cctcttccga gcacttacaa    180

cgtctccatg tgctcggaat cgttctggtg cggcggcgtc gaaatccgct acccgttcta    240

tcttgccaac gcaaccgccg actacagcgg gagctactac tcctgcggct acaccgactt    300

gagcgtttcc tgcaaactcg aggtcgaggg gccgacgacg acatggaccc ctaccatccg    360

tctcggcggc gacaactaca ccgtcaagaa catcttgtac gactatcata ccatctcact    420

ggcggacagc gatgtgctcg gaggcggcga gtgccccgtc gtccaccaca acgtcagctt    480

cgacgagacg tggctgcaca accccagcgc cttcgacaac ctcaccttct tcttcggatg    540

ccactggggg ccacgcgata cactgcctga atttgccggc aacaacatca gctgcgccgg    600

gttcagtact ccagctatca gcggtggagg ctccttcgtg ttcaagcctg aagatcttga    660

cgaacatgcg gagcaggagt tggcttcaca ctgcgacgag gttttctccg tgccagtgag    720

aagcgaggct ctgcagcagg cgatcgtcag caacctcagc ctcggggacg ggtacggcga    780

gctgcttagg caggggatcg agttggaatg gaaacggaca tcggaggatc agtgtggcca    840

gtgcgaggaa tcgggctccg gcggacggtg cgcctacagc cagaagagag aattccttgg    900

ctgcttgtgc agcggaggga aggcgggcaa cccgttctgc aaaccatcaa gatcaaaaag    960

gaaagaagca tctattgttg gtgctgttgc cgttgcattc ctgtgtctag tcattctcac   1020

atgcttcttg gcttgtagac atggttcgct gcccttcaaa tcggagaaca aaccagggac   1080

aaggattgag tccttcctac agaagaacga gagtatacat ccgaaaagat acacctacac   1140

ggacgtgaaa agaatgacaa aatccttcgc tgtgaagcta ggccaaggtg ggtttggtgc   1200

tgtatacaaa ggcagcctcc acgatggccg acaggtagca gtcaagatgc tcaaggacac   1260

ccaaggtgac ggcgaggaat tcatgaacga ggtggctagc atcagcagga cttctcatgt   1320

caacgtcgtg acacttctag ggttttgctt gcaagggtcg aaaagagcac tgatctacga   1380

gtacatgccc aatggttcgc tcgaaaggta tgccttcacc ggtgacatga acagtgagaa   1440

tttgctaacc tgggaaaggc tatttgacat agcaattggc acggccagag ggctcgaata   1500

cctacaccgg ggatgcaaca ctcggatcgt gcattttgac atcaagccac acaacatcct   1560

gttagaccag gatttctgtc ctaagatctc tgactttgga ctggccaagc tatgtctgaa   1620

caaagagagc gctatctcca ttgttggcgc aagagggacg atagggtata tcgccccgga   1680

ggtctactca aagcaatttg gaacaatcag cagcaagtct gatgtctata gctatgggat   1740

gatggtcctt gagatggttg gagcaaggga aaggaataca agcgcaagcg cagatagtga   1800

ccatagcagc caatatttcc ctcagtggat ttatgaacat ttggacgact attgtgttgg   1860

tgcttccgag attaatggtg agaccacaga gctcgtgagg aagatgatag ttgtaggtct   1920
```

```
gtggtgcata caagtgattc cgactgatcg accaacaatg acgagagtcg tcgagatgtt   1980

ggaagggagc acgagtaatc tagagttgcc acccagagtt ctcttgagct gacaaagcgt   2040

agatattttt cctatcaaat g                                             2061


<210> SEQ ID NO 97
<211> LENGTH: 666
<212> TYPE: PRT
<213> ORGANISM: Zea mays

<400> SEQUENCE: 97

Met Ala Ala His Leu Pro Arg Leu Pro Val Leu Leu Leu Val Leu Leu
1               5                   10                  15

Ala Ala His Val Val Ser Thr Ser Ala His Ala Glu Pro Pro Leu Pro
            20                  25                  30

Ser Pro Tyr Ser Thr Ser Ala His Gly Glu Pro Pro Leu Pro Ser Thr
        35                  40                  45

Tyr Asn Val Ser Met Cys Ser Glu Ser Phe Trp Cys Gly Gly Val Glu
    50                  55                  60

Ile Arg Tyr Pro Phe Tyr Leu Ala Asn Ala Thr Ala Asp Tyr Ser Gly
65                  70                  75                  80

Ser Tyr Tyr Ser Cys Gly Tyr Thr Asp Leu Ser Val Ser Cys Lys Leu
                85                  90                  95

Glu Val Glu Gly Pro Thr Thr Thr Trp Thr Pro Thr Ile Arg Leu Gly
            100                 105                 110

Gly Asp Asn Tyr Thr Val Lys Asn Ile Leu Tyr Asp Tyr His Thr Ile
        115                 120                 125

Ser Leu Ala Asp Ser Asp Val Leu Gly Gly Gly Glu Cys Pro Val Val
    130                 135                 140

His His Asn Val Ser Phe Asp Glu Thr Trp Leu His Asn Pro Ser Ala
145                 150                 155                 160

Phe Asp Asn Leu Thr Phe Phe Phe Gly Cys His Trp Gly Pro Arg Asp
                165                 170                 175

Thr Leu Pro Glu Phe Ala Gly Asn Asn Ile Ser Cys Ala Gly Phe Ser
            180                 185                 190

Thr Pro Ala Ile Ser Gly Gly Gly Ser Phe Val Phe Lys Pro Glu Asp
        195                 200                 205

Leu Asp Glu His Ala Glu Gln Glu Leu Ala Ser His Cys Asp Glu Val
    210                 215                 220

Phe Ser Val Pro Val Arg Ser Glu Ala Leu Gln Gln Ala Ile Val Ser
225                 230                 235                 240

Asn Leu Ser Leu Gly Asp Gly Tyr Gly Glu Leu Leu Arg Gln Gly Ile
                245                 250                 255

Glu Leu Glu Trp Lys Arg Thr Ser Glu Asp Gln Cys Gly Gln Cys Glu
            260                 265                 270

Glu Ser Gly Ser Gly Gly Arg Cys Ala Tyr Ser Gln Lys Arg Glu Phe
        275                 280                 285

Leu Gly Cys Leu Cys Ser Gly Gly Lys Ala Gly Asn Pro Phe Cys Lys
    290                 295                 300

Pro Ser Arg Ser Lys Arg Lys Glu Ala Ser Ile Val Gly Ala Val Ala
305                 310                 315                 320

Val Ala Phe Leu Cys Leu Val Ile Leu Thr Cys Phe Leu Ala Cys Arg
                325                 330                 335

His Gly Ser Leu Pro Phe Lys Ser Glu Asn Lys Pro Gly Thr Arg Ile
```

-continued

```
            340                 345                 350

Glu Ser Phe Leu Gln Lys Asn Glu Ser Ile His Pro Lys Arg Tyr Thr
        355                 360                 365

Tyr Thr Asp Val Lys Arg Met Thr Lys Ser Phe Ala Val Lys Leu Gly
    370                 375                 380

Gln Gly Gly Phe Gly Ala Val Tyr Lys Gly Ser Leu His Asp Gly Arg
385                 390                 395                 400

Gln Val Ala Val Lys Met Leu Lys Asp Thr Gln Gly Asp Gly Glu Glu
                405                 410                 415

Phe Met Asn Glu Val Ala Ser Ile Ser Arg Thr Ser His Val Asn Val
            420                 425                 430

Val Thr Leu Leu Gly Phe Cys Leu Gln Gly Ser Lys Arg Ala Leu Ile
        435                 440                 445

Tyr Glu Tyr Met Pro Asn Gly Ser Leu Glu Arg Tyr Ala Phe Thr Gly
    450                 455                 460

Asp Met Asn Ser Glu Asn Leu Leu Thr Trp Glu Arg Leu Phe Asp Ile
465                 470                 475                 480

Ala Ile Gly Thr Ala Arg Gly Leu Glu Tyr Leu His Arg Gly Cys Asn
                485                 490                 495

Thr Arg Ile Val His Phe Asp Ile Lys Pro His Asn Ile Leu Leu Asp
            500                 505                 510

Gln Asp Phe Cys Pro Lys Ile Ser Asp Phe Gly Leu Ala Lys Leu Cys
        515                 520                 525

Leu Asn Lys Glu Ser Ala Ile Ser Ile Val Gly Ala Arg Gly Thr Ile
    530                 535                 540

Gly Tyr Ile Ala Pro Glu Val Tyr Ser Lys Gln Phe Gly Thr Ile Ser
545                 550                 555                 560

Ser Lys Ser Asp Val Tyr Ser Tyr Gly Met Met Val Leu Glu Met Val
                565                 570                 575

Gly Ala Arg Glu Arg Asn Thr Ser Ala Ser Ala Asp Ser Asp His Ser
            580                 585                 590

Ser Gln Tyr Phe Pro Gln Trp Ile Tyr Glu His Leu Asp Asp Tyr Cys
        595                 600                 605

Val Gly Ala Ser Glu Ile Asn Gly Glu Thr Thr Glu Leu Val Arg Lys
    610                 615                 620

Met Ile Val Val Gly Leu Trp Cys Ile Gln Val Ile Pro Thr Asp Arg
625                 630                 635                 640

Pro Thr Met Thr Arg Val Val Glu Met Leu Glu Gly Ser Thr Ser Asn
                645                 650                 655

Leu Glu Leu Pro Pro Arg Val Leu Leu Ser
            660                 665
```